US010072084B2

(12) United States Patent
Bigner et al.

(10) Patent No.: US 10,072,084 B2
(45) Date of Patent: Sep. 11, 2018

(54) DUAL SPECIFIC IMMUNOTOXIN FOR BRAIN TUMOR THERAPY

(71) Applicants: Duke University, Durham, NC (US); THE UNITED STATES OF AMERICA AS REPRESENTED BY THE SECRETARY OF HEALTH AND HUMAN SERVICES, NATIONAL INSTITUTES OF HEALTH, Washington, DC (US)

(72) Inventors: Darell D. Bigner, Mebane, NC (US); Chien-Tsun Kuan, Cary, NC (US); Ira H. Pastan, Potomac, MD (US); Charles Pegram, Durham, NC (US)

(73) Assignees: Duke University, Durham, NC (US); The United States of America as Represented by the Secretary Department of Health and Human Services (NIH), Washington, DC (US)

( * ) Notice: Subject to any disclaimer, the term of this patent is extended or adjusted under 35 U.S.C. 154(b) by 39 days.

(21) Appl. No.: 15/290,040

(22) Filed: Oct. 11, 2016

(65) Prior Publication Data
US 2017/0051064 A1 Feb. 23, 2017

Related U.S. Application Data

(60) Division of application No. 14/270,836, filed on May 6, 2014, now Pat. No. 9,492,564, which is a division of application No. 13/482,406, filed on May 29, 2012, which is a continuation of application No. 12/418,975, filed on Apr. 6, 2009.

(60) Provisional application No. 61/044,190, filed on Apr. 11, 2008.

(51) Int. Cl.
| | |
|---|---|
| *C07K 16/28* | (2006.01) |
| *A61K 39/395* | (2006.01) |
| *C07K 14/21* | (2006.01) |
| *A61K 47/68* | (2017.01) |
| *A61K 39/00* | (2006.01) |
| *A61K 38/00* | (2006.01) |

(52) U.S. Cl.
CPC .... *C07K 16/2863* (2013.01); *A61K 39/39558* (2013.01); *A61K 47/6829* (2017.08); *A61K 47/6849* (2017.08); *C07K 14/21* (2013.01); *A61K 38/00* (2013.01); *A61K 2039/505* (2013.01); *A61K 2039/545* (2013.01); *C07K 2317/56* (2013.01); *C07K 2317/565* (2013.01); *C07K 2317/622* (2013.01); *C07K 2317/624* (2013.01); *C07K 2317/92* (2013.01); *C07K 2319/04* (2013.01); *C07K 2319/55* (2013.01)

(58) Field of Classification Search
None
See application file for complete search history.

(56) References Cited

PUBLICATIONS

Boskovitz et al. (World federation of neuron-oncology second quadrennial meeting and the sixth meeting of the European association for neuro-oncology Edinburgh, United Kingdom, Jul. 2005; Abstract #346, p. 370) (Year: 2005).*
Stockwin et al. (Drug Discovery and Design, vol. 31(2), p. 433-6, Apr. 2003) (Year: 2003).*
Di Paolo et al. (Clin Cancer Res., vol. 9(7),pp. 2837-2848, Jul. 2003) (Year: 2003).*
Mathias Schmidt et al., "Suppression of metastasis formation by a recombinant single chain antibody-toxin targeted to full-length and oncogenic variant EGF receptors," Oncogene, 1999; 18: 1711-21, Anti-EGFRwt/EGFRvIII, Immunotoxin for Glioblastoma Therapy.
B. Neyns et al., "Stratified phase II trial of cetuximab in patients with recurrent high-grade glioma," Annals of Oncology, 2009; 20: 1596-603.
Aaron S. Gajadhar et al., "In situ analysis of mutant EGFR's prevalent in gliblastoma multiforme reveals aberrant dimerization, activation, and differential responses to anit-EGFR targeted therapy," Molecular Cancer Research, 2012; 10: 428-40.
Johns TG et al., "Novel Monoclonal antibody specific for the del-7 epidermal growth factor receptor (EGFR) that also recognizes the EGFR expressed in cells containing amplification of the EGFR gene," International journal of cancer, Journal international du cancer, 2002; 98:398-408. Abstract Only.
H. Masui et al., "Growth Inhibition of Human Tumor Cells in Athymic Mice by Anti-Epidermal Growth Factor Receptor Monoclonal Antibodies," Cancer Research, 1987; 44:1002-7.
RM Perera et al., "Treatment of Human Tumor Xenografts with Monoclonal Antibody 806 in Combination with a Prototypical Epidermal Growth Factor Receptor-Specific Antibody Generates Enhances Antitumor Activity," Clinical Cancer Research, 2005; 11:6390-9.
Boskovitz et al. (World federation of neuron-oncology second quadrennial meeting and the sixth meeting of the European association for neuro-oncology Edinburgh, United Kingdom, Jul. 2005, Abstract #346, p. 370).
Stockwin et al. (Drug Discovery and Design, vol. 31(2), p. 433-6, Apr. 2003).
Di Paolo et al. (Clinical Cancer Res., vol. 9(7), pp. 2837-2848, Jul. 2003).

(Continued)

*Primary Examiner* — Laura B Goddard
*Assistant Examiner* — Meera Natarajan
(74) *Attorney, Agent, or Firm* — Banner & Witcoff, Ltd

(57) ABSTRACT

We tested the in vitro and in vivo efficacy of a recombinant bispecific immunotoxin that recognizes both EGFRwt and tumor-specific EGFRvIII receptors. A single chain antibody was cloned from a hybridoma and fused to toxin, carrying a C-terminal peptide which increases retention within cells. The binding affinity and specificity of the recombinant bispecific immunotoxin for the EGFRwt and the EGFRvIII proteins was measured. In vitro cytotoxicity was measured. In vivo activity of the recombinant bispecific immunotoxin was evaluated in subcutaneous models and compared to that of an established monospecific immunotoxin. In our preclinical studies, the bispecific recombinant immunotoxin, exhibited significant potential for treating brain tumors.

13 Claims, 30 Drawing Sheets

Specification includes a Sequence Listing.

(56) References Cited

PUBLICATIONS

C. J. Wikstrand, et al., "Monoclonal Antibodies Against EGFRvIII Are Tumor Specific and React With Breast and Lung Carcinomas and Malignant Gliomas," Cancer Research, Jul. 15, 1995, vol. 55, pp. 3140-3148.

D. Andres et al., Variants of the Carboxyl-Terminal KDEL Sequence Direct Intracellular Retention, The Journal of Biological Chemistry, Apr. 15, 1990, vol. 265, No. 11, pp. 5952-5955.

V. Chandramohann et al., Dual-Specific Antibody, D2C7 (scdsFv)-PE38KDEL, for Brain Tumor Therapy, 13th International Symposium on Pediatric Neuro-Oncology, Jun. 29-Jul. 2, 2008, Publication Date Apr. 12, 2008.

\* cited by examiner

Fig. 1A) V_H

EVHLQQSGPELEKPGASVKISCKASGYSFT GYNMN VKQSNGKSLEWIG
                                 CDR1
NIDPYYGDTDYDQKFKG TLTADKSSNTVYMQLQSLTSEDSAVYYCAR
      CDR2
GAHRDYYAMDY WGQGTSVTVSS
   CDR3

Fig. 1B) V_L

DIQMTQSPASLSASVGETVTITC RTSENIYIYLA WYQQKQGKSPQLLVY
                           CDR1
NAKTLAE GVPSRFSGSGSGTQFSLKINGLQPEDFGGYYC QQHYGTPYT
 CDR2                                      CDR3
FGGGTKLEKK

EGFRwt peptide $K_A = 6.3 \times 10^8 \text{ M}^{-1}$ and $K_D = 1.6 \times 10^{-9}$ M EGFRvIII peptide $K_A = 7.8 \times 10^8 \text{ M}^{-1}$ and $K_D = 1.3 \times 10^{-9}$ M

NR6W
- anti-Tac-PE38KDEL
- D2C7-PE38 IC$_{50}$ 3.1 ng
- scds-D2C7-PE38KDEL IC$_{50}$ 0.690 n
- dsFv-MR1-1-PE38KDEL IC$_{50}$ 48 ng

Fig. 5C

NR6M
- anti-Tac-PE38KDEL
- D2C7-PE38 IC$_{50}$ 6.0 ng
- scds-D2C7-PE38KDEL IC$_{50}$ 1.4 ng
- dsFv-MR1-1-PE38KDEL IC$_{50}$ 2.6 ng

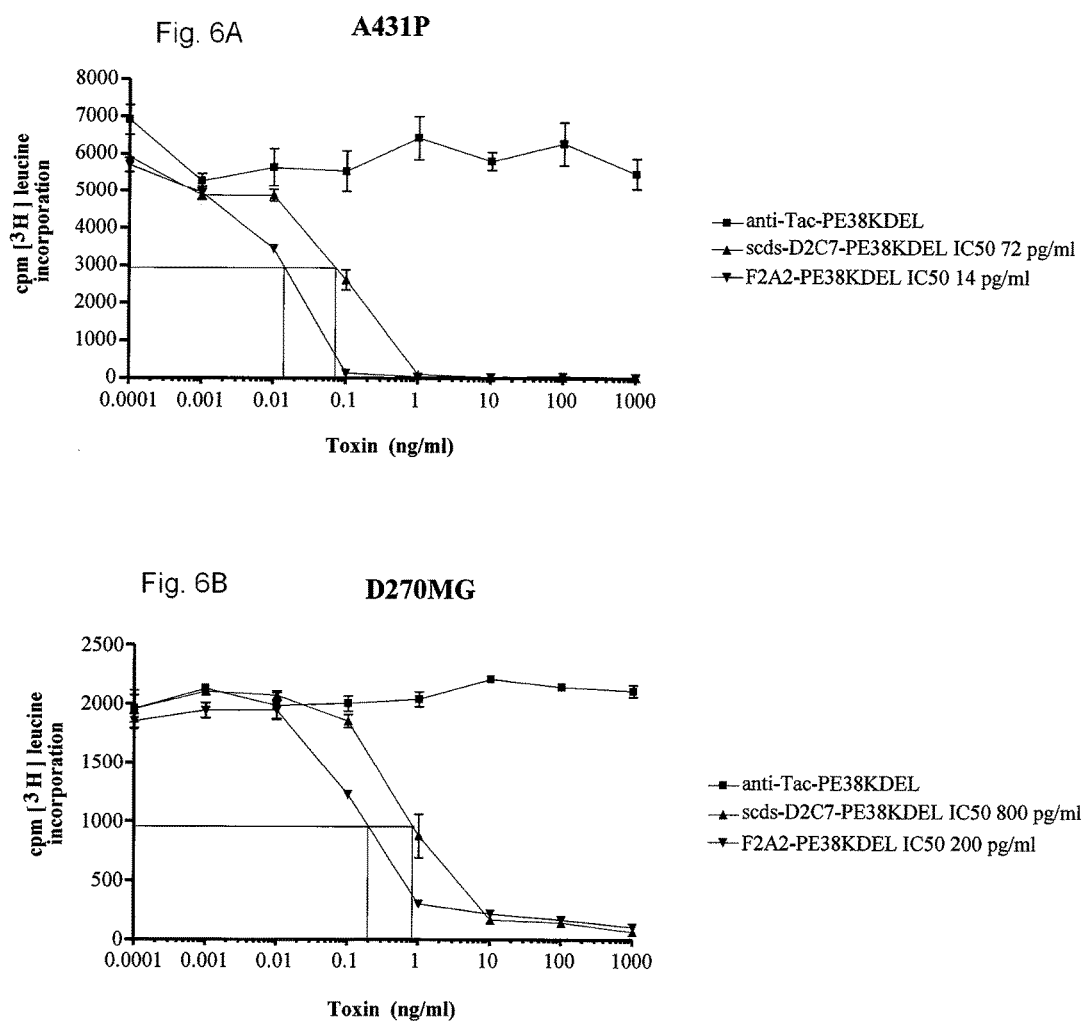

F2A2 cytotoxicity on NR6, NR6W and NR6M
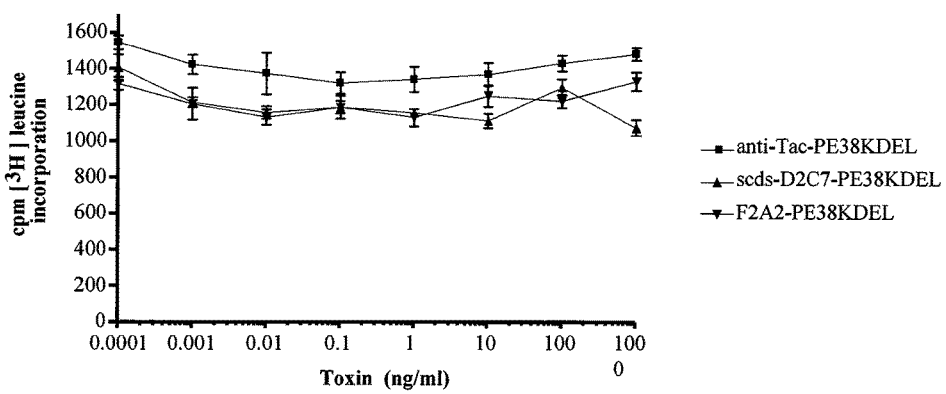
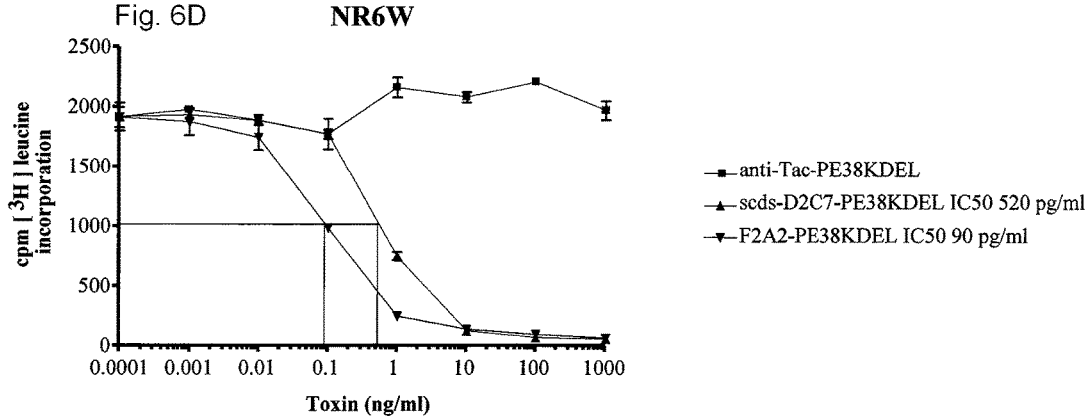
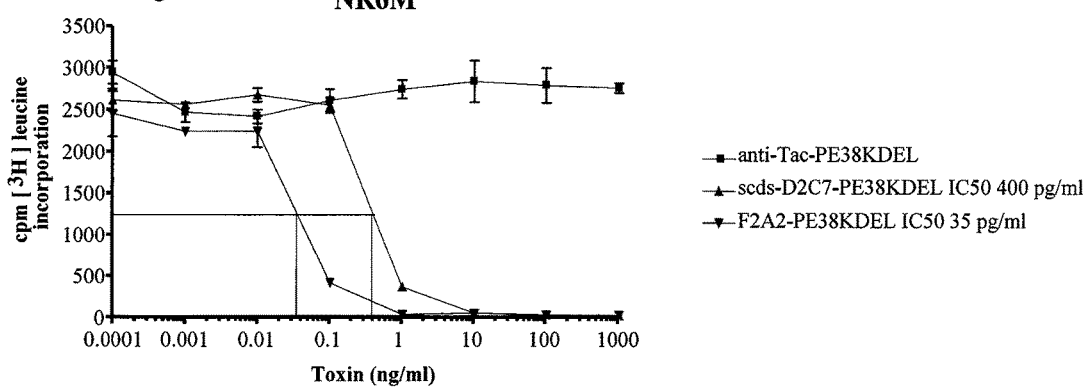

D2C7 (EGFR wt AND EGFRvIII) EXPRESSION
Q1-TUMOR ANTIGEN (TA); Q2-TA+CD133; Q3-NEGATIVE, Q4-CD133

08-0647p3(NORMOXIC) 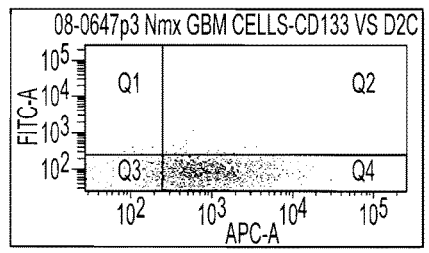

| SPECIMEN NAME: | 08-0647p3 NMX G... |  |
|---|---|---|
| TUBE NAME: | CD133 VS D2C7 |  |
| POPULATION | #EVENTS | %PARENT |
| Q1 | 6 | 0.4 |
| Q2 | 27 | 1.8 |
| Q3 | 232 | 15.2 |
| Q4 | 1,259 | 82.6 |

08-0647p4(HYPOXIC) 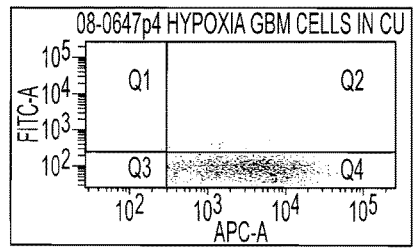

| SPECIMEN NAME: | 08-0647p4 HYPOXIA... |  |
|---|---|---|
| TUBE NAME: | CD133 VS D2C7 |  |
| POPULATION | #EVENTS | %PARENT |
| Q1 | 1 | 0.1 |
| Q2 | 16 | 1.0 |
| Q3 | 93 | 6.0 |
| Q4 | 1,436 | 92.9 |

08-0624p3(NORMOXIC) 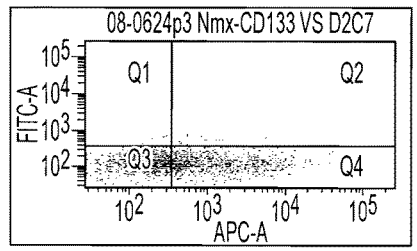

| SPECIMEN NAME: | 08-0624p3 NMX |  |
|---|---|---|
| TUBE NAME: | CD133 vs D2C7 |  |
| POPULATION | #EVENTS | %PARENT |
| Q1 | 4 | 0.2 |
| Q2 | 14 | 0.8 |
| Q3 | 865 | 52.1 |
| Q4 | 777 | 46.8 |

08-0624p2(HYPOXIC) 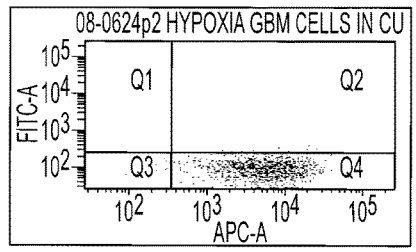

| SPECIMEN NAME: | 08-0624p2 HYPOXIA GBM C... |  |
|---|---|---|
| TUBE NAME: | CD133 VS D2C7 |  |
| POPULATION | #EVENTS | %PARENT |
| Q1 | 0 | 0.0 |
| Q2 | 12 | 1.1 |
| Q3 | 16 | 1.4 |
| Q4 | 1,079 | 97.5 |

FIG. 7B

F2A2 (EGFR wt AND EGFRvIII) EXPRESSION
Q1-TUMOR ANTIGEN (TA); Q2-TA+CD133; Q3-NEGATIVE, Q4-CD133

08-0647p3(NORMOXIC)
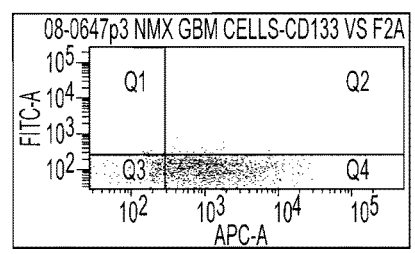

| SPECIMEN NAME: | 08-0647p3 NMX G... | |
|---|---|---|
| TUBE NAME: | CD133 VS F2A2 | |
| POPULATION | #EVENTS | %PARENT |
| Q1 | 6 | 0.4 |
| Q2 | 20 | 1.3 |
| Q3 | 274 | 17.6 |
| Q4 | 1,258 | 80.7 |

08-0647p4(HYPOXIC)
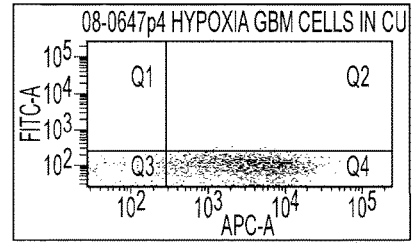

| SPECIMEN NAME: | 08-0647p4 HYPOXIA... | |
|---|---|---|
| TUBE NAME: | CD133 VS F2A2 | |
| POPULATION | #EVENTS | %PARENT |
| Q1 | 0 | 0.0 |
| Q2 | 10 | 0.6 |
| Q3 | 106 | 6.9 |
| Q4 | 1,425 | 92.5 |

08-0624p3(NORMOXIC)
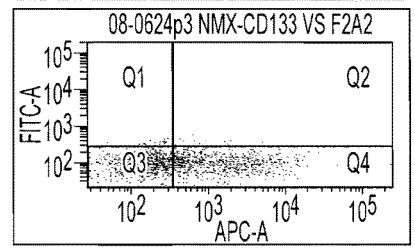

| SPECIMEN NAME: | 08-0624p3 NMX | |
|---|---|---|
| TUBE NAME: | CD133 VS F2A2 | |
| POPULATION | #EVENTS | %PARENT |
| Q1 | 17 | 1.0 |
| Q2 | 16 | 0.9 |
| Q3 | 895 | 51.3 |
| Q4 | 818 | 46.8 |

08-0624p2(HYPOXIC)
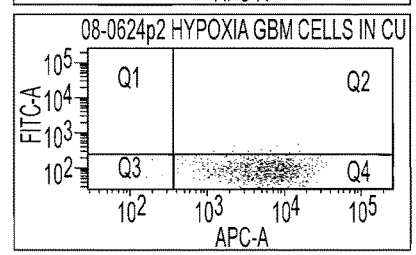

| SPECIMEN NAME: | 08-0624p2 HYPOXIA GBM C... | |
|---|---|---|
| TUBE NAME: | CD133 VS F2A2 | |
| POPULATION | #EVENTS | %PARENT |
| Q1 | 0 | 0.0 |
| Q2 | 12 | 1.3 |
| Q3 | 5 | 0.5 |
| Q4 | 902 | 98.2 |

FIG. 7F

F2A2 (EGFR wt AND EGFRvIII) EXPRESSION
Q1-TUMOR ANTIGEN (TA); Q2-TA+CD133; Q3-NEGATIVE, Q4-CD133
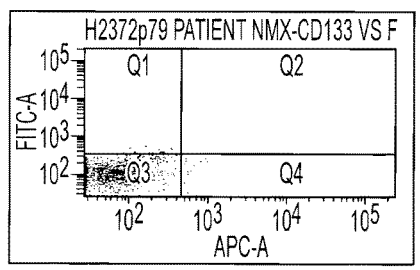
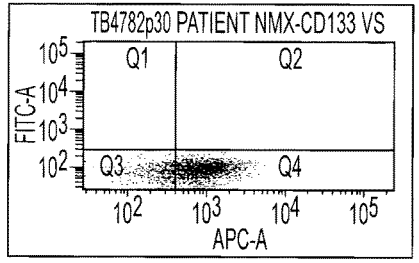
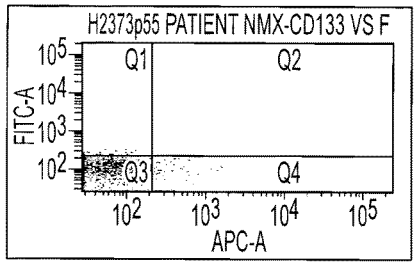
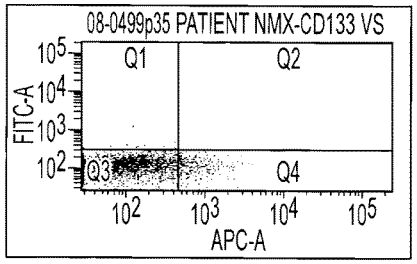
FIG. 7H

D2C7 (EGFR wt AND EGFRvIII) EXPRESSION
Q1-TUMOR ANTIGEN (TA); Q2-TA+CD133; Q3-NEGATIVE, Q4-CD133
2224p55/6 NORMOXIC
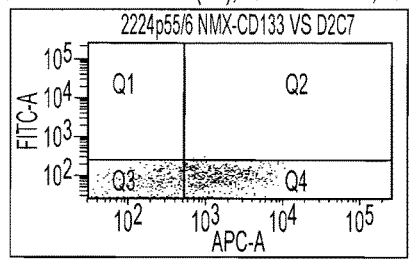
2224p55/5 HYPOXIC
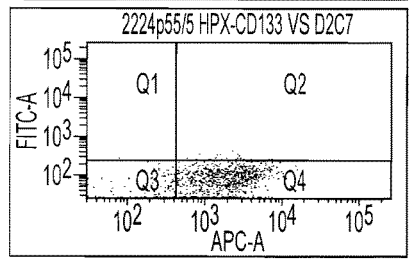
661p136/2 NORMOXIC
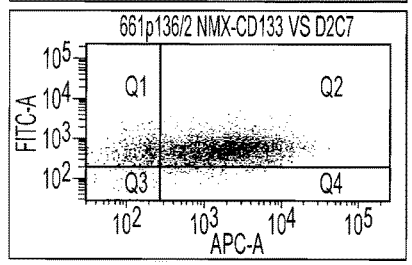
661p136/4 HYPOXIC
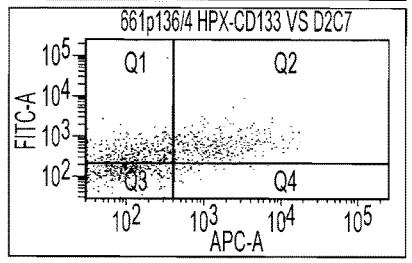
717p39/6 NORMOXIC
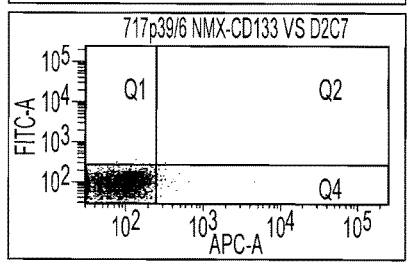
717p39/6 HYPOXIC
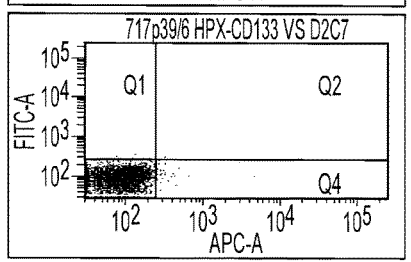
FIG. 7K

F2A2 (EGFR wt AND EGFRvIII) EXPRESSION
Q1-TUMOR ANTIGEN (TA); Q2-TA+CD133; Q3-NEGATIVE, Q4-CD133

2224p55/6 NORMOXIC
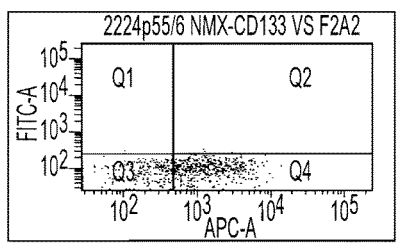

| SPECIMEN NAME: | 2224p55/6 NMX | |
|---|---|---|
| TUBE NAME: | CD133 VS F2A2 | |
| POPULATION | #EVENTS | %PARENT |
| Q1 | 1 | 0.1 |
| Q2 | 3 | 0.3 |
| Q3 | 361 | 40.7 |
| Q4 | 522 | 58.9 |

2224p55/5 HYPOXIC
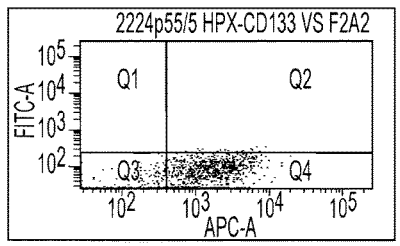

| SPECIMEN NAME: | 2224p55/5 HPX | |
|---|---|---|
| TUBE NAME: | CD133 VS F2A2 | |
| POPULATION | #EVENTS | %PARENT |
| Q1 | 0 | 0.0 |
| Q2 | 16 | 1.8 |
| Q3 | 119 | 13.4 |
| Q4 | 754 | 84.8 |

661p136/2 NORMOXIC
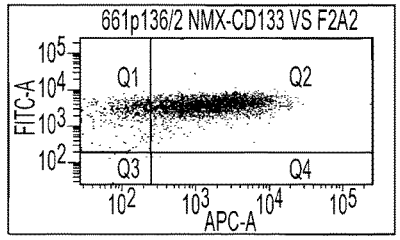

| SPECIMEN NAME: | 661p136/2 NMX | |
|---|---|---|
| TUBE NAME: | CD133 VS F2A2 | |
| POPULATION | #EVENTS | %PARENT |
| Q1 | 450 | 11.2 |
| Q2 | 3,537 | 88.2 |
| Q3 | 18 | 0.4 |
| Q4 | 3 | 0.1 |

661p136/4 HYPOXIC
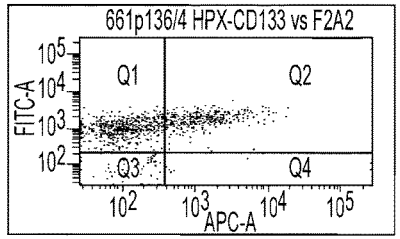

| SPECIMEN NAME: | 661p136/4 HPX | |
|---|---|---|
| TUBE NAME: | CD133 VS F2A2 | |
| POPULATION | #EVENTS | %PARENT |
| Q1 | 587 | 58.3 |
| Q2 | 348 | 34.6 |
| Q3 | 61 | 6.1 |
| Q4 | 10 | 1.0 |

717p39/6 NORMOXIC
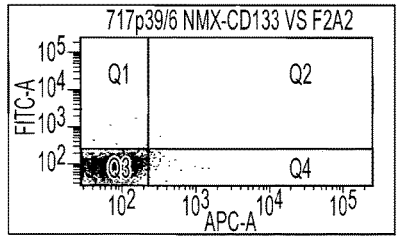

| SPECIMEN NAME: | 717p39/6 NMX | |
|---|---|---|
| TUBE NAME: | CD133 VS F2A2 | |
| POPULATION | #EVENTS | %PARENT |
| Q1 | 9 | 0.2 |
| Q2 | 2 | 0.0 |
| Q3 | 4,582 | 99.0 |
| Q4 | 37 | 0.8 |

717p39/6 HYPOXIC
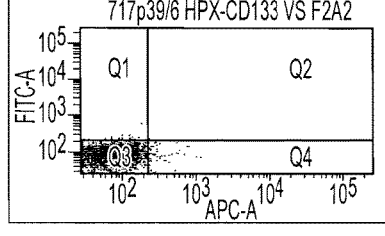

| SPECIMEN NAME: | 717p39/6 HPX | |
|---|---|---|
| TUBE NAME: | CD133 VS F2A2 | |
| POPULATION | #EVENTS | %PARENT |
| Q1 | 15 | 0.4 |
| Q2 | 2 | 0.1 |
| Q3 | 3,340 | 97.9 |
| Q4 | 55 | 1.6 |

FIG. 7P

D2C7 (EGFR wt AND EGFRvIII) EXPRESSION
Q1-TUMOR ANTIGEN (TA); Q2-TA+CD133; Q3-NEGATIVE, Q4-CD133
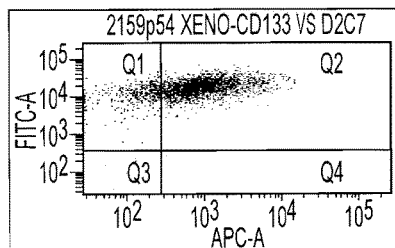
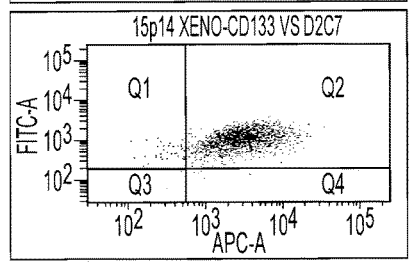
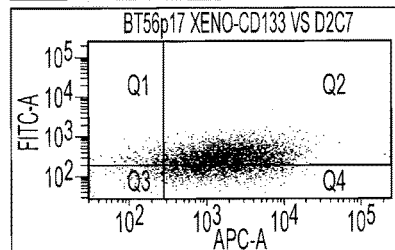
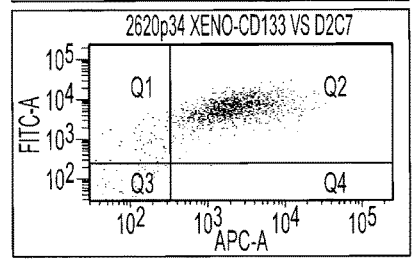
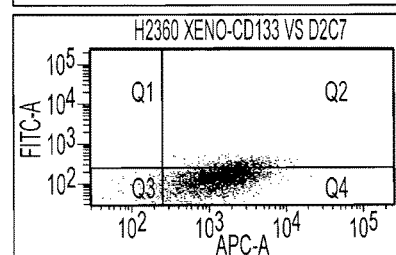
FIG. 7Q D2C7 (EGFR wt AND EGFRvIII) EXPRESSION
Q1-TUMOR ANTIGEN (TA); Q2-TA+CD133; Q3-NEGATIVE, Q4-CD133
2322p9 XENOGRAFT 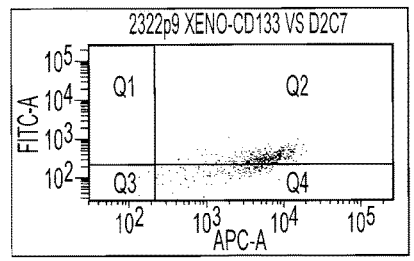
212p117 XENOGRAFT 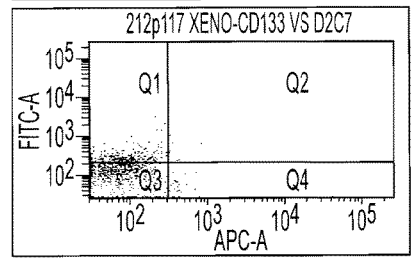
456p130 XENOGRAFT 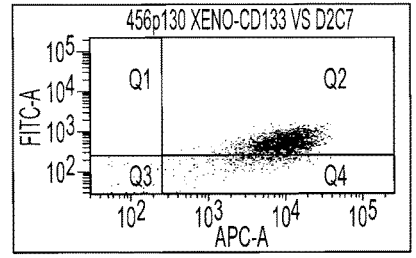
561p7 XENOGRAFT 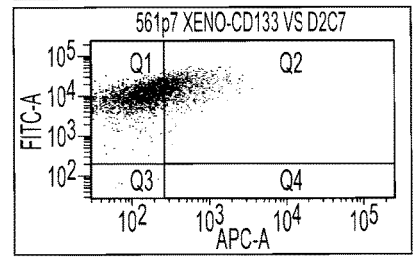
601p8 XENOGRAFT 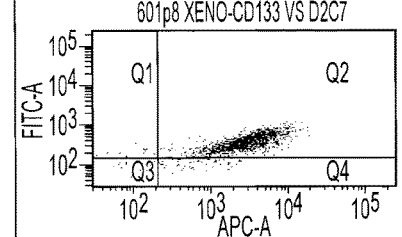
FIG. 7R

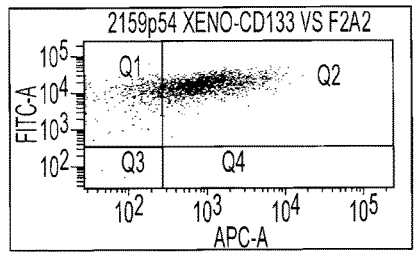
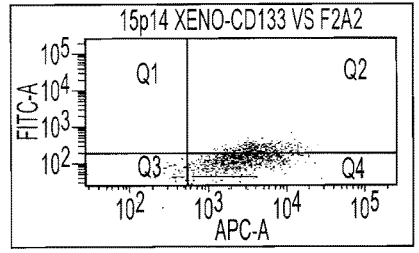
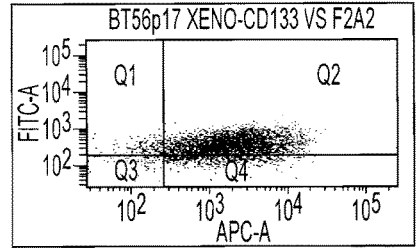
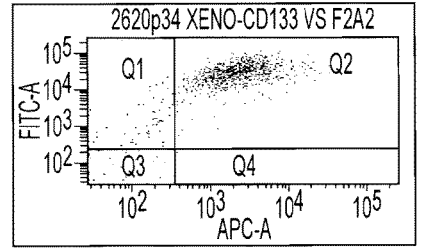
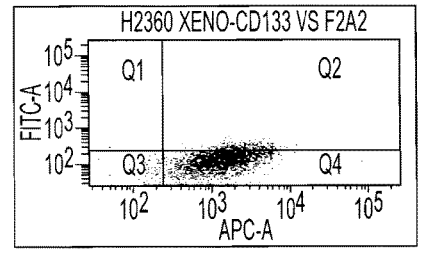
FIG. 7T

F2A2 (EGFR wt AND EGFRvIII) EXPRESSION
Q1-TUMOR ANTIGEN (TA); Q2-TA+CD133; Q3-NEGATIVE, Q4-CD133

2322p9 XENOGRAFT 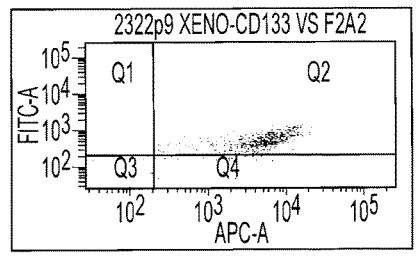

| SPECIMEN NAME: | 2322p9 XENO | |
|---|---|---|
| TUBE NAME: | CD133 VS F2A2 | |
| POPULATION | #EVENTS | %PARENT |
| Q1 | 0 | 0.0 |
| Q2 | 680 | 91.6 |
| Q3 | 10 | 1.3 |
| Q4 | 52 | 7.0 |

212p117 XENOGRAFT 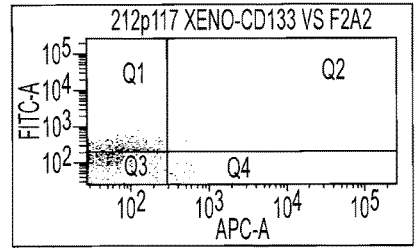

| SPECIMEN NAME: | 212p117 XENO | |
|---|---|---|
| TUBE NAME: | CD133 VS F2A2 | |
| POPULATION | #EVENTS | %PARENT |
| Q1 | 313 | 25.3 |
| Q2 | 3 | 0.2 |
| Q3 | 883 | 71.5 |
| Q4 | 36 | 2.9 |

456p130 XENOGRAFT 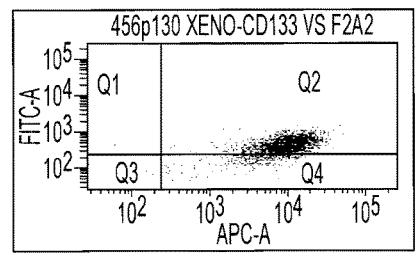

| SPECIMEN NAME: | 456p130 XENO | |
|---|---|---|
| TUBE NAME: | CD133 VS F2A2 | |
| POPULATION | #EVENTS | %PARENT |
| Q1 | 1 | 0.0 |
| Q2 | 2,566 | 82.7 |
| Q3 | 11 | 0.4 |
| Q4 | 523 | 16.9 |

561p7 XENOGRAFT 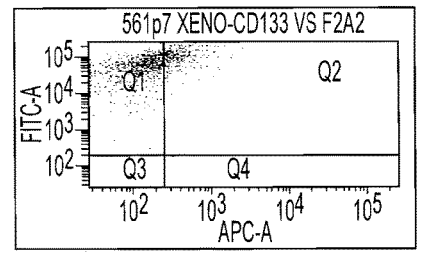

| SPECIMEN NAME: | 561p7 XENO | |
|---|---|---|
| TUBE NAME: | CD133 VS F2A2 | |
| POPULATION | #EVENTS | %PARENT |
| Q1 | 807 | 65.7 |
| Q2 | 420 | 34.2 |
| Q3 | 1 | 0.1 |
| Q4 | 0 | 0.0 |

601p8 XENOGRAFT 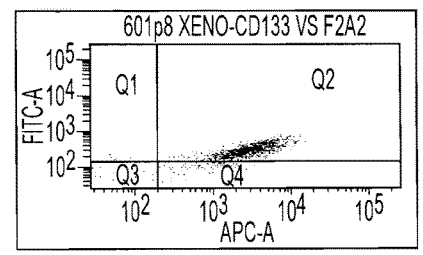

| SPECIMEN NAME: | 601p8 XENO | |
|---|---|---|
| TUBE NAME: | CD133 VS F2A2 | |
| POPULATION | #EVENTS | %PARENT |
| Q1 | 6 | 0.4 |
| Q2 | 1,441 | 88.7 |
| Q3 | 27 | 1.7 |
| Q4 | 151 | 9.3 |

FIG. 7U

F2A2 (EGFR wt AND EGFRvIII) EXPRESSION
Q1-TUMOR ANTIGEN (TA); Q2-TA+CD133; Q3-NEGATIVE, Q4-CD133
717p36 XENOGRAFT 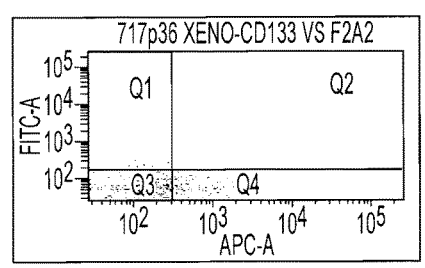
645p65 XENOGRAFT 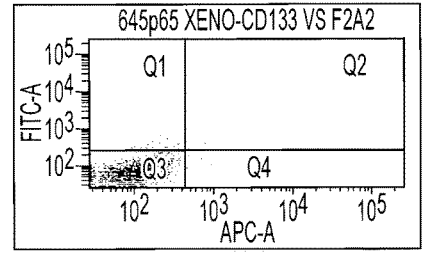
661p136 XENOGRAFT 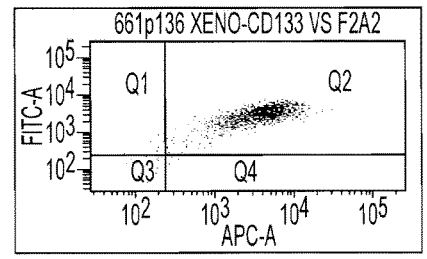
FIG. 7V

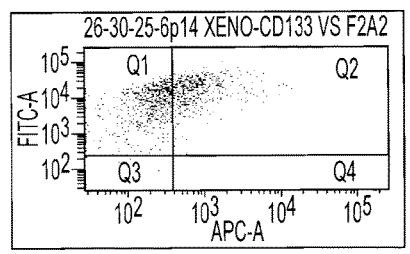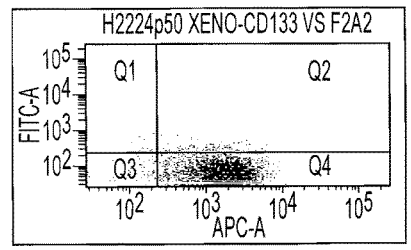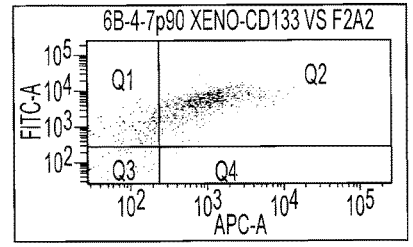
FIG. 7W

SEQUENCE LISTING

<160> NUMBER OF SEQ ID NOS: 13

<210> SEQ ID NO 1
<211> LENGTH: 117
<212> TYPE: PRT
<213> ORGANISM: Mus musculus

<400> SEQUENCE: 1

Glu Val His Leu Gln Gln Ser Gly Pro Glu Leu Glu Lys Pro Gly Ala
 1               5                  10                  15

Ser Val Lys Ile Ser Cys Lys Ala Ser Gly Tyr Ser Phe Thr Gly Tyr
            20                  25                  30

Asn Met Asn Val Lys Gln Ser Asn Gly Lys Ser Leu Glu Trp Ile Gly
        35                  40                  45

Asn Ile Asp Pro Tyr Tyr Gly Asp Thr Asp Tyr Asn Gln Lys Phe Lys
    50                  55                  60

Gly Thr Leu Thr Ala Asp Lys Ser Ser Asn Thr Val Tyr Met Gln Leu
65                  70                  75                  80

Gln Ser Leu Thr Ser Glu Asp Ser Ala Val Tyr Tyr Cys Ala Arg Gly
                85                  90                  95

Ala His Arg Asp Tyr Tyr Ala Met Asp Tyr Trp Gly Gln Gly Thr Ser
            100                 105                 110

Val Thr Val Ser Ser
        115

<210> SEQ ID NO 2
<211> LENGTH: 107
<212> TYPE: PRT
<213> ORGANISM: Mus musculus

<400> SEQUENCE: 2

Asp Ile Gln Met Thr Gln Ser Pro Ala Ser Leu Ser Ala Ser Val Gly
 1               5                  10                  15

Glu Thr Val Thr Ile Thr Cys Arg Thr Ser Glu Asn Ile Tyr Ile Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Gly Leu Gln Pro
65                  70                  75                  80

Glu Asp Phe Gly Tyr Tyr Cys Gln Gln His Tyr Gly Thr Pro Tyr
                85                  90                  95

Thr Phe Gly Gly Gly Thr Lys Leu Glu Lys Lys
            100                 105

<210> SEQ ID NO 3
<211> LENGTH: 5
<212> TYPE: PRT
<213> ORGANISM: Mus musculus

```
<400> SEQUENCE: 3

Gly Tyr Asn Met Asn
1               5

<210> SEQ ID NO 4
<211> LENGTH: 17
<212> TYPE: PRT
<213> ORGANISM: Mus musculus

<400> SEQUENCE: 4

Asn Ile Asp Pro Tyr Tyr Gly Asp Thr Asp Tyr Asp Gln Lys Phe Lys
1               5                   10                  15

Gly

<210> SEQ ID NO 5
<211> LENGTH: 11
<212> TYPE: PRT
<213> ORGANISM: Mus musculus

<400> SEQUENCE: 5

Gly Ala His Arg Asp Tyr Tyr Ala Met Asp Tyr
1               5                   10

<210> SEQ ID NO 6
<211> LENGTH: 11
<212> TYPE: PRT
<213> ORGANISM: Mus musculus

<400> SEQUENCE: 6

Arg Thr Ser Glu Asn Ile Tyr Ile Tyr Leu Ala
1               5                   10

<210> SEQ ID NO 7
<211> LENGTH: 7
<212> TYPE: PRT
<213> ORGANISM: Mus musculus

<400> SEQUENCE: 7

Asn Ala Lys Thr Leu Ala Glu
1               5

<210> SEQ ID NO 8
<211> LENGTH: 9
<212> TYPE: PRT
<213> ORGANISM: Mus musculus

<400> SEQUENCE: 8

Gln Gln His Tyr Gly Thr Pro Tyr Thr
1               5

<210> SEQ ID NO 9
<211> LENGTH: 23
<212> TYPE: DNA
<213> ORGANISM: Mus musculus

<400> SEQUENCE: 9
ctggacaggg atccagagtt cca                                           23

<210> SEQ ID NO 10
<211> LENGTH: 24
<212> TYPE: DNA
<213> ORGANISM: Mus musculus
```

<400> SEQUENCE: 10
ctcattcctg ttgaagctct tgac                                              24

<210> SEQ ID NO 11
<211> LENGTH: 15
<212> TYPE: PRT
<213> ORGANISM: Artificial Sequence
<220> FEATURE:
<223> OTHER INFORMATION: synthetic linker

<400> SEQUENCE: 11

Gly Gly Gly Gly Ser Gly Gly Gly Gly Ser Gly Gly Gly Gly Ser
 1               5                  10                  15

<210> SEQ ID NO 12
<211> LENGTH: 747
<212> TYPE: DNA
<213> ORGANISM: Artficial sequence
<220> FEATURE:
<223> OTHER INFORMATION: single chain variable region fragment of F2A2

<400> SEQUENCE: 12
gaagtgcagc tggtagagtc tgggggaggc ttagtgaggc tggagggtc cctgaaactc         60 tcctgtgcag cctctggatt cactttcagt gactattaca tgtattgggt tcgccagact       120
ccggaaaaga ggctggagtg ggtcgcaagc attagtggtg gtgatgatta cacctactac       180
tcagagagtg tgaaggggcg attcaccatc tccagagaca atgccaagaa caccctgtgc       240
ctccaaatga acagtctgaa gtctgacgac acagccatgt attactgtgt tagaggagag       300
gggaggaact gggacgacta tgctatggac tattggggtc aaggaacttc agtcaccgtc       360
tcctcgggtg gtggcggttc aggcggaggt ggctctggcg gtggcggatc ggatattgtg       420
atgacccaaa ctccactctc cctgcctgtc agtcttggag atcaagcctc catctcttgc       480
agatctagtc agagccttgt acacactcat ggacacacct atttacattg gcacctgcag       540
aagccaggcc agtctccaaa gctcctgatc tataaagttt ccaaccgatt ttctggggtc       600
ccagacaggt tcagtggcag tggatcaggg acagatttca cactcaagat cagcagagtg       660
gaggctgagg atctgggagt ttatttctgc tctcaaagta cacatgttcc tcggacgttc       720
ggtggaggca ccaagctgga aatcaaa                                          747

<210> SEQ ID NO 13
<211> LENGTH: 249
<212> TYPE: PRT
<213> ORGANISM: Artificial Sequence
<220> FEATURE:
<223> OTHER INFORMATION: single chain variable region fragment F2A2

<400> SEQUENCE: 13

Glu Val Gln Leu Val Glu Ser Gly Gly Gly Leu Val Arg Pro Gly Gly
 1               5                  10                  15

Ser Leu Lys Leu Ser Cys Ala Ala Ser Gly Phe Thr Phe Ser Asp Tyr
             20                  25                  30

Tyr Met Tyr Trp Val Arg Gln Thr Pro Glu Lys Arg Leu Glu Trp Val
         35                  40                  45

Ala Ser Ile Ser Gly Gly Asp Asp Tyr Thr Tyr Tyr Ser Glu Ser Val
     50                  55                  60

Lys Gly Arg Phe Thr Ile Ser Arg Asp Asn Ala Lys Asn Thr Leu Cys
 65                  70                  75                  80

Leu Gln Met Asn Ser Leu Lys Ser Asp Asp Thr Ala Met Tyr Tyr Cys

-continued

```
                    85                      90                      95
Val Arg Gly Glu Gly Arg Asn Trp Asp Asp Tyr Ala Met Asp Tyr Trp
                100                     105                 110

Gly Gln Gly Thr Ser Val Thr Val Ser Ser Gly Gly Gly Gly Ser Gly
            115                     120                 125

Gly Gly Gly Ser Gly Gly Gly Gly Ser Asp Ile Val Met Thr Gln Thr
        130                     135                 140

Pro Leu Ser Leu Pro Val Ser Leu Gly Asp Gln Ala Ser Ile Ser Cys
145                     150                 155                 160

Arg Ser Ser Gln Ser Leu Val His Thr His Gly His Thr Tyr Leu His
                165                     170                 175

Trp His Leu Gln Lys Pro Gly Gln Ser Pro Lys Leu Leu Ile Tyr Lys
            180                     185                 190

Val Ser Asn Arg Phe Ser Gly Val Pro Asp Arg Phe Ser Gly Ser Gly
        195                     200                 205

Ser Gly Thr Asp Phe Thr Leu Lys Ile Ser Arg Val Glu Ala Glu Asp
    210                     215                 220

Leu Gly Val Tyr Phe Cys Ser Gln Ser Thr His Val Pro Arg Thr Phe
225                     230                 235                 240

Gly Gly Gly Thr Lys Leu Glu Ile Lys
                245
```

DUAL SPECIFIC IMMUNOTOXIN FOR BRAIN TUMOR THERAPY

This application claims the benefit of provisional application Ser. No. 61/044,190 filed Apr. 11, 2008, the contents of which are expressly incorporated herein.

TECHNICAL FIELD OF THE INVENTION

This invention is related to the area of anti-tumor immunotoxins. In particular, it relates to an immunotoxin specific for two tumor-associated antigens.

BACKGROUND OF THE INVENTION

Gliomas are the most common primary tumors of the central nervous system (CNS) {Louis, 1995}. Glioblastoma multiforme (GBM) is the most frequent and the most malignant type of glioma. There is a much higher incidence of GBM in adults than in children. According to the Central Brain Tumor Registry of the United States statistical report, GBM accounts for about 20% of all brain tumors in the USA (CBTRUS, 19982002). Current treatment for patients with GBM include, surgery followed by radiation and chemotherapy. Despite intensive research the median survival for GBM patients until the early 1990s was less than a year {Walker, 1978}. The single most important advance in the treatment of these tumors over the past 30 years has been the introduction of temozolomide, initially in combination with external beam irradiation, and then followed by repetitive cycles of temozolomide alone {Stupp, 2007}. However, this has increased the overall median survival by only 75 days. Clearly, new and more efficient therapeutic approaches are needed to improve GBM patient survival. Monoclonal antibodies (mAbs), either armed (fused to immunotoxin [IT] or radioisotopes) or unarmed, are presently a rapidly growing category of new drug entities. This is well demonstrated by the large number of mAb-based clinical trials currently in progress for brain tumor patients. Boskovitz, A., Wikstrand, C. J., Kuan, C. T., Zalutsky, M. R., Reardon, D. A., and Bigner, D. D. Monoclonal antibodies for brain tumour treatment. Expert Opin Biol Ther, 4: 1453-1471, 2004. More recently, genetically engineered single-chain variable-region antibody fragments (scFvs), consisting of the heavy- and light-chain variable regions ($V_H$ and $V_L$) fused to toxins and targeting antigens expressed specifically by brain tumor, are under investigation. Archer, G. E., Sampson, J. H., Lorimer, I. A., McLendon, R. E., Kuan, C. T., Friedman, A. H., Friedman, H. S., Pastan, I. H., and Bigner, D. D. Regional treatment of epidermal growth factor receptor vIII-expressing neoplastic meningitis with a single-chain immunotoxin, MR-1. Clin Cancer Res, 5: 2646-2652, 1999. Because it is small, an scFv-IT fusion protein should have greater tumor penetration than an intact IgG and therefore lead to enhanced therapeutic efficacy {Pastan, 1995}.

The epidermal growth factor receptor (EGFR) is a 170-kDa, transmembrane receptor tyrosine kinase (RTK). It is stimulated by binding of its ligands, such as transforming growth factor (TGF)-a or EGF, to its extracellular domain. Ligand binding induces receptor dimerization and activates a tyrosine-specific protein kinase activity {Ushiro, 1980} involved in controlling epithelial cell growth and proliferation. Ultimately, the receptor-ligand complexes are internalized, and the EGFR signal is terminated. EGFR overexpression is frequently observed in a wide variety of human cancers, including breast {Klijn, 1992; Osaki, 1992}, lung {Pavelic, 1993}, head and neck {Rubin Grandis, 1996}, prostate {Fox, 1994}, bladder {Chow, 2001}, colorectal {Yasui, 1988}, and ovarian carcinoma {Bartlett, 1996}, as well as brain tumors {Arita, 1989; Libermann, 1984}. In contrast, the level of EGFR in normal brain is undetectable or extremely low. EGFR is the most frequently amplified gene in GBM {Fuller, 1992}. Correlating with the gene amplification, the protein is overexpressed in about 60% to 90% of GBM cases. In the absence of gene amplification, protein overexpression has also been observed in 12% to 38% of GBM patients {Chaffanet, 1992}, which could be due to aberrant translational and post-translational mechanisms. Preclinical studies have shown that EGFR activation, in addition to protecting cells from apoptosis, also induces several tumorigenic processes, including proliferation, angiogenesis, and metastasis {Huang, 1999}.

EGFR gene amplification is often associated with gene rearrangements. Several EGFR deletion mutants have been identified {Rasheed, 1999}, the most common one being EGFRvIII, which is present in 20% to 50% of GBMs with EGFR amplification. Wikstrand, C. J., Fung, K. M., Trojanowski, J. Q., McLendon, R. E., and Bigner, D. D. Antibodies and molecular immunology: immunohistochemistry and antigens of diagnostic significance. In: D. D. Bigner, R. E. McLendon, and J. M. Bruner (eds.), Russell and Rubinstein's Pathology of the Nervous System, 6th edition, pp. 251-304. New York: Oxford University Press, 1998. The mutant EGFRvIII contains a deletion of exon 2-7 of the EGFR gene, which is characterized by an in-frame deletion of 801 base pairs of the coding region {Sugawa, 1990}. This deletion creates a novel glycine residue at the fusion junction at position 6, between amino acid residues 5 and 274, generating a tumor-specific protein sequence that is expressed specifically on tumor cells but not on normal tissues. EGFRvIII is a constitutively active RTK which is not further activated by EGFR ligands. Batra, S. K., Castelino-Prabhu, S., Wikstrand, C. J., Zhu, X., Humphrey, P. A., Friedman, H. S., and Bigner, D. D. Epidermal growth factor ligand-independent, unregulated, cell-transforming potential of a naturally occurring human mutant EGFRvIII gene. Cell Growth Differ, 6: 1251-1259, 1995. EGFRvIII is widely expressed in malignant gliomas {Humphrey, 1990} and carcinomas, including head and neck {Sok, 2006} and breast. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., and et al. Monoclonal antibodies against EGFRvIII are tumor specific and react with breast and lung carcinomas and malignant gliomas. Cancer Res, 55: 3140-3148, 1995. Overexpression of EGFRvIII induces resistance in glioma cells to commonly used chemotherapeutic agents {Nagane, 1998}.

Monoclonal antibodies targeting either the wild-type EGFR (EGFRwt) or EGFRvIII have been developed. One of them, D2C7, a murine IgG1κ, was developed by our group. The D2C7 hybridoma recognizes both the EGFRwt and the tumor-specific EGFRvIII receptors {Boskovitz, 2005}.

There is a continuing need in the art for effective means of treating brain tumors and prolonging life of affected patients.

SUMMARY OF THE INVENTION

According to one embodiment of the invention a single chain variable region antibody is provided. The antibody binds with a binding affinity that is at least $5 \times 10^8$ $M^{-1}$ as measured by surface plasmon resonance to both (a) EGFR found on normal human cells and (b) EGFR variant III mutant.

According to another embodiment a method is provided of treating a tumor in a human. A single chain variable region antibody is administered to the human. The antibody binds with a binding affinity that is at least $5\times10^8$ M-1 as measured by surface plasmon resonance to both (a) EGFR found on normal human cells and (b) EGFR variant III mutant. Tumor cells are thereby killed.

According to yet another embodiment of the invention a monoclonal antibody is provided that binds with a binding affinity that is at least $5\times10^8$ $M^{-1}$ to both (a) EGFR found on normal human cells and (b) EGFR variant III mutant. The antibody has a $V_H$ sequence as shown in FIG. 1A (SEQ ID NO: 1), a $V_L$ sequence as shown in FIG. 1B (SEQ ID NO: 2), or CDR1, CDR2, and CDR3 regions as shown in FIGS. 1A (SEQ ID NO: 3, 4, 5) and 1B (SEQ ID NO: 6, 7, 8).

Yet another embodiment of the invention provides a monoclonal antibody that binds with a binding affinity that is at least $1\times10^8$ $M^{-1}$ to both (a) EGFR found on normal human cells and (b) EGFR variant III mutant. The antibody is selected from the group consisting of F2A2 and B10B11.

An additional embodiment of the invention provides a method of determining a therapeutic plan to treat a tumor in a human. Tissue of the tumor is contacted with an antibody that binds with a binding affinity that is at least $1\times10^8$ $M^{-1}$ to both (a) EGFR found on normal human cells and (b) EGFR variant III mutant. The amount of cells in the tissue that bind to the antibody is determined. Greater amounts of cells which bind are a positive factor to recommend using the antibody therapeutically for the patient.

These and other embodiments which will be apparent to those of skill in the art upon reading the specification provide the art with methods and reagents for treating brain tumors.

BRIEF DESCRIPTION OF THE DRAWINGS

FIG. 1A-1B. Deduced amino acid sequence of D2C7 scFv cloned from D2C7 hybridoma. $V_H$ (FIG. 1A) and $V_L$ (FIG. 1B) antigen-binding regions of D2C7 scFv. Amino acid numbering and CDR (underlined) delimitation were determined according to the IMGT database.

(FIG. 4A) Parental NR6 (NIH 3T3 murine fibroblast) cells used as control. Indirect FACS analysis demonstrates the reactivity of D2C7 (scdsFv)-PE38KDEL immunotoxin with cells expressing (FIG. 4B) EGFRwt (NR6W) or (FIG. 4C) EGFRvIII (NR6M). Cells were stained with D2C7 (scdsFv)-PE38KDEL (grey open peaks) or a non-specific scFv (anti-Tac-PE38KDEL) control (filled black peaks).

FIG. 5A-5C. In vitro cytotoxicity assay of D2C7 (scdsFv)-PE38KDEL on (FIG. 5A) NR6, (FIG. 5B) NR6W, and (FIG. 5C) NR6M cells. The cytotoxic effect of D2C7-PE38 (▲) and D2C7 (scdsFv)-PE38KDEL (●) was compared to that of an established EGFRvIII-specific scFv immunotoxin, MR1-1-(scdsFv)-PE38KDEL (x). A non-specific scFv anti-Tac-PE38 (■) was used as a control. At least three different assays were performed for each cell line, and results from one representative experiment are shown.

FIG. 6A-6E. In vitro cytotoxicity of F2A2 on A431P and D270MG (FIG. 6A-6B) and on NR6, NR6W, and NR6M (FIG. 6C-6E).

DETAILED DESCRIPTION OF THE INVENTION

Figure 2:
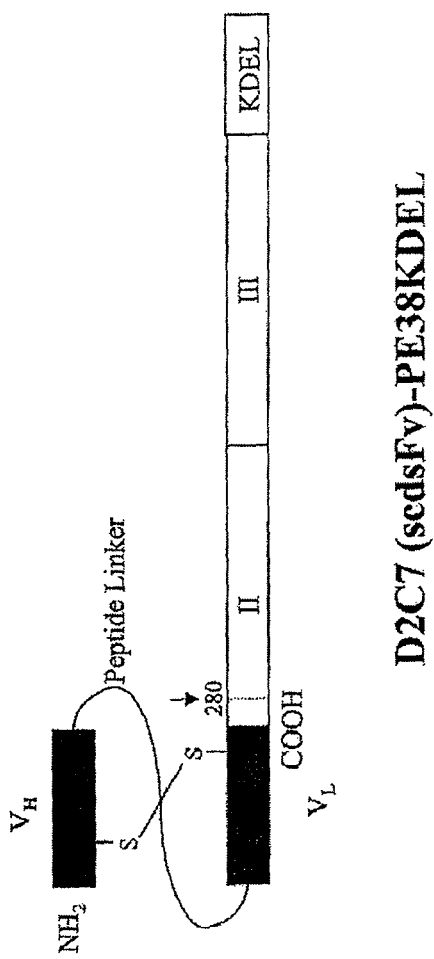
FIG. 2. Schematic of D2C7 (scdsFv)-PE38KDEL. The arrow marks the proteolytic site of PE for activation. S-S shows the disulfide bond linkage between the Fv fragments. II, PE domain II for translocation; III, PE domain III for ADP-ribosylation of EF2, KDEL, for increased endoplasmic reticulum retention.

It is a discovery of the present inventors that antibodies can bind with comparable and high affinities to both EGFR found on normal cells and to EGFR variant III. By virtue of binding to both forms of EGFR, these antibodies can induce cytotoxicity in a higher percentage of cells within a tumor. Moreover, high affinity binding of the antibodies to the cell surface receptors permits and enhances antibody internalization, again increasing their cytotoxic effect.

Antibodies which have been identified which have excellent properties in this regard include D2C7, F2A2, B10B11, and H11 (Life Span Biosciences, Inc. Seattle, Wash.). These are mouse monoclonal antibodies produced by hybridomas. These antibodies can be "converted" into other forms, for example, humanized, chimeric, and single chain variable region antibodies. These conversions are well known in the art and typically involve cloning of the antibody encoding genes from the hybridomas which produced the mouse monoclonal antibodies. If the VH or VL or the CDR region sequences remain the same as in the original monoclonal antibody, then the antibody may have retain binding specificity.

Such antibodies and "converted" antibodies can be bound, either covalently or non-covalently, to other useful moieties. For example, they can be conjugated to radionuclides or radioactive moieties. They can be joined to a biological toxin, such as Pseudomanas exotoxin A, ricin, or diphtheria toxin. They can be conjugated to chemotherapeutic agents. They can be joined to other antibodies. Attachments of the antibodies to other moieties can occur by means of genetic engineering, if the other moiety is a protein, so that a fusion protein is produced in a host cell. The attachments may be done chemically, in vitro. The attachments may be covalent or non-covalent. Non-covalent attachments preferably use strong biological specific binding pairs to achieve strong attachments. For diagnostic purposes, the antibodies can be attached to chromophores, or other easily detectable moieties.

Other moieties which can be attached to the antibodies include those to provide additional beneficial properties. For example, a KDEL (lys-asp-glu-leu) tetra-peptide can be added at the carboxy-terminus of the protein to provide retention in the endoplasmic reticulum. Variants such as DKEL, RDEL, and KNEL which function similarly can also be used.

Binding affinities can be measured by any means known in the art. One particular method employs surface plasmon resonance. Binding affinities within one log for wild-type and mutant EGFRvIII are desirable, as are those within 50%, 75%, and 90% of each other. Binding to cells can be measured, for example by flow cytometry. Association and dissociation rates can be determined. Affinity constants can be calculated. The kinetics of binding may be a significant factor in cytotoxicity in the body. Binding affinities may be at least $1 \times 10^8$ M$^{-1}$, at least $5 \times 10^8$ M$^{-1}$, at least $1 \times 10^9$ M$^{-1}$, or at least $5 \times 10^9$ M$^{-1}$. Techniques can be used to "affinity mature" i.e., improve affinity of, candidate antibodies.

Tumors which can be treated include those in which at least one EGFRvIII allele is present. These may be found in breast, head and neck, brain, glioblastoma multiforme, astrocytoma, lung, or other tumors. It may be desirable to determine the presence of such an allele prior to therapy. This can be done using a oligonucleotide-based technique, such as PCR, or using an immunological technique, such as immunohistochemistry. It may be desirable to determine the amount, fraction, ratio, or percentage of cells in the tumor which express EGFR and/or EGFRvIII. The more cells which express EGFR on their surfaces, the more beneficial such antibody therapy is likely to be.

Antibodies and antibody constructs and derivatives can be administered by any technique known in the art. Compartmental delivery may be desirable to avoid cytotoxicity for normal tissues that express EGFR. Suitable compartmental delivery methods include, but are not limited to delivery to the brain, delivery to a surgically created tumor resection cavity, delivery to a natural tumor cyst, and delivery to tumor parenchyma.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods
Cell Lines.

Cell lines expressing EGFRwt used were the human epidermoid carcinoma cell line A431 {Merlino, 1984} and the murine Swiss 3T3 mouse fibroblast cell line EGFRwt transfectant NR6W {Batra, 1995}. Cell lines transfected to express EGFRvIII included the murine Swiss 3T3 mouse fibroblast cell line-derived transfectant NR6M {Batra, 1995}. The parental murine Swiss 3T3 mouse fibroblast cell line, NR6, was used as control. All cell lines were cultured in complete zinc option-10% fetal bovine serum (FBS) (Richter's zinc option; Invitrogen, San Diego, Calif.) and passed at confluence using 0.05% Trypsin-EDTA (Invitrogen).

Disaggregation of Xenograft Tumor Samples.

Xenograft tissues from malignant glioma (D256MG, D270MG, D2159MG) obtained under sterile conditions from the Duke animal facility were prepared for cell culture in a laminar flow hood with a sterile technique. Tumor material was finely minced with scissors and added to a trypsinizing flask with approximately 10 ml of 100 µg Liberase (Roche Indianapolis, Ind.). This mixture was stirred at 37° C. for 10 min, and a cell-rich supernatant was obtained. The dissociated cells were filtered through a steel sieve with 100 mesh wire. The reaction was inhibited with the addition of the ovomucoid solution. The cells were washed with complete medium and pelleted at 1000 rpm for 5 min. The cell suspension was further treated with Ficoll-Hypaque to remove any red blood cells and then washed once in complete media. The cells were cultured and passaged until sufficient numbers were obtained (first adherent population, p0; subsequent passages, p1, p2, and so forth). The attached cells were harvested with 0.05% Trypsin-EDTA.

Cloning of Variable Heavy ($V_H$) and Variable Light ($V_L$) Domains of the D2C7 mAb.

Total cellular mRNA was isolated from 106 hybridoma cells by using a Dynabeads, mRNA direct kit (Invitrogen). VH and VL cDNAs of the D2C7 mAb were obtained by a RACE method using a SMART RACE cDNA amplification kit (Clontech, Palo Alto, Calif.). In brief, adaptor-ligated cDNA was generated from 300 ng of the mRNA by using PowerScript Reverse Transcriptase and SMART II A oligonucleotide (Clontech), along with 12 µM each of 3' end primers designed to anneal the heavy-chain (HC) and light-chain (LC) constant region sequence of immunoglobulin (mouseIgG1/2: 5'-CTGGACAGGGATCCAGAGTTCCA-3' (SEQ ID NO: 9) and mouseLC: 5'-CTCATTCCTGTT-GAAGCTCTTGAC-3'; SEQ ID NO: 10). The primers covered the constant region sequences registered in the Kabat database. The prepared cDNAs were used as the templates for PCR reactions between 5' end primer which binds to the adaptor sequence and the immunoglobulin HC- and LC-specific 3' end primer specified above. The obtained sequences were aligned and verified according to the Kabat alignment scheme. The $V_H$ domain was fused to the $V_L$ domain by a 15-amino-acid peptide (Gly$_4$Ser)$_3$ (SEQ ID NO: 11) linker by PCR. The D2C7 scFv fragment was cloned into pRK79 vector using a T4 DNA ligase kit (Pierce Biotechnology, Rockford, Ill.). The D2C7 (scdsFv) construct was obtained by mutating residues 44 of $V_H$ and 100 of $V_L$ by site-directed mutagenesis using a QuickChange Multi-Site Directed Mutagenesis Kit (Stratagene, La Jolla, Calif.). The D2C7-(scdsFv)-PE38KDEL IT was obtained by ligating the D2C7 (scdsFv) PCR fragment into pRB199 vector, and the sequence was verified. The MR1-1-(scdsFv)-PE38KDEL IT was obtained by ligating the MR1-1 (scdsFv) PCR fragment into pRB199 vector, and the sequence was verified.

Preparation of Recombinant Immunotoxins.

The different D2C7 ITs were generated by fusing the specific scFv with the sequences for domains II and III of Pseudomonas exotoxin A (PE38) according to the protocol described previously {Buchner, 1992}. The specific scFv IT was expressed under control of the T7 promoter in E. coli BL21 (X DE3) (Stratagene, La Jolla, Calif.). All recombinant proteins accumulated in the inclusion bodies. The ITs were then reduced, refolded, and further purified as a monomer (64 kDa) by ion exchange and size exclusion chromatography to greater than 95% purity.

Surface Plasmon Resonance (Biacore Analysis).

Binding kinetic profiles of purified D2C7-(scdsFv)-PE38KDEL IT were measured by surface plasmon resonance by using a Biacore 3000 biosensor system (Pharmacia, Uppsala, Sweden). As an antigen, either EGFRwt extracellular domain (ECD) or EGFRvIII ECD proteins were immobilized on the surface of the CM5 sensor chip at pH 5.5. Test samples were diluted in running buffer (10 mM HEPES/150 mM NaCl/3.4 mM EDTA, pH 7.4) and passed over the chip at concentrations from 25 to 200 nM. The association and dissociation rate constants and the average affinity were determined by using the nonlinear curve-fitting BIAevaluation software (Pharmacia).

Flow Cytometry.

Indirect FACS analysis was performed with D2C7-(scdsFv)-PE38KDEL IT. Briefly, 1×10$^6$ cells (NR6, NR6W, or NR6M) were suspended in 500|j, 1 of PBS (Invitrogen)

containing 5% FBS (Invitrogen) (5% FBS/PBS). The D2C7-(scdsFv)-PE38KDEL IT or negative control, anti-Tac(scFv)-PE38 (a gift from Dr. Ira Pastan), was added to the cells at a concentration of 10 J·g/ml, and the samples were incubated for 40 min. After washing, cells were incubated with rabbit anti-*Pseudomonas* exotoxin A antibody (Sigma, St. Louis, Mo.) followed by labeling with FITC-conjugated goat anti-rabbit IgG antibody (Zymed, South San Francisco, Calif.). To prevent internalization of target antigens during assays, all the reagents and buffers were kept on ice, and experiments were performed at 4° C. Stained cells were analyzed on a Becton Dickinson FACSort instrument equipped with CellQuest software (Becton Dickinson, San Jose, Calif.).

In Vitro Cell Killing Assay.

The cytotoxicity of the ITs on cultured cell lines and cells isolated from xenografts was assayed by inhibition of protein synthesis as described previously {Beers, 2000}. Cells were seeded in 96-well plates at a density of 2×104 cells per well in 200 µl of complete zinc option medium 24 h before the assay. Immunotoxins were serially diluted to achieve a final concentration of 0.01 to 1000 ng/ml in PBS containing 0.2% bovine serum albumin (BSA; 0.2% BSA/PBS), and 10 µl of diluted toxin was added to each well. Plates were incubated for 20 h at 37° C. and then pulsed with 1 µCi/well of L-[4,5-3H]leucine (Amersham Biosciences, Buckinghamshire, UK) in 25 µl of 0.2% BSA/PBS for 3 h at 37° C. Radiolabeled cells were captured on filter-mats and counted in a MicroBeta scintillation counter (PerkinElmer, Shelton, Conn.). The cytotoxic activity of an IT was defined by IC50, which was the toxin concentration that suppressed incorporation of radioactivity by 50% as compared to the radioactivity measured in cells that were not treated with toxin.

Determination of Nonspecific Toxicity in Mice.

The single-dose mouse $LD_{40}$ was determined by using female BALB/c mice (6-8 weeks old, 20 g), which were given a single intraperitoneal (i.p.) injection of different doses of D2C7-(scdsFv)-PE38KDEL IT (0.25 to 1.25 mg/kg) diluted in 200 il of PBS containing 0.2% human serum albumin (PBS-HSA). Mice were observed for 2 weeks following IT injection.

In Vivo Tumor Model.

Female athymic nude mice (approximately 20 g body weight, 4-6 weeks of age) were injected subcutaneously (s.c.) in the right flank with 3×106 A431 or NR6M cells suspended in 50 µl of PBS. A total of 8 to 10 mice per arm were randomly selected for inoculation when the implanted tumors reached a median tumor volume of 200 to 300 mm3. Mice were treated with three doses of 0.3 mg/kg of D2C7-(scdsFv)-PE38KDEL IT or MR1-1-(scdsFv)-PE38KDEL IT diluted in 0.2% PBS-HSA, by i.p. injections every other day. The control mice were handled in the same manner and treated with 0.2% PBS-HSA. Tumors were measured twice weekly with a handheld vernier caliper, and the tumor volumes were calculated in cubic millimeters by using the formula: ([length]×[width2])/2. Animals were tested out of the study when tumor volume met both of the following criteria: 1) larger than 1000 mm3, and 2) 5 times its original treatment size.

Assessment of Response.

The response of the s.c. xenografts was assessed by delay in the growth of tumor in mice treated with drug as compared with growth in control mice (T−C). The growth delay was the difference between the median times required for tumors in treated (T) and control (C) mice to reach five times the size at the initiation of therapy and at least greater than 1000 mm³. Tumor regression was defined as a decrease in tumor volume over two successive measurements.

Statistical analysis was performed using the Wilcoxon rank-sum test for growth delay and Fisher's exact test for tumor regressions as previously described {Friedman, 1994}.

Example 2

Cloning of the $V_H$ and $V_L$ Domain of D2C7 IgG1κ.

$V_H$ and $V_L$ cDNAs were isolated from the D2C7 hybridoma by a RACE method as described in "Materials and Methods." The heavy-chain and light-chain variable domains were cloned and sequenced. The amplified $V_H$ and $V_L$ fragments were approximately 360 and 321 bp, respectively. The deduced amino acid sequences of the D2C7 $V_H$ and $V_L$ domains are shown in FIG. 1. Sequence analysis of the $V_H$ and $V_L$ amino acids, using the database of germ-line genes (http://www.ncbi.nlm.nih.gov/igblast/), revealed that the sequences were derived from different germ-line V genes with a similarity of 70% to 75%.

Example 3

Construction, Expression, and Purification of D2C7-(scdsFv)-PE38KDEL Immunotoxin.

The carboxyl terminus of the D2C7 $V_H$ domain was connected to the amino terminus of the $V_L$ domain by a 15-amino-acid peptide $(Gly_4Ser)_3$ linker (SEQ ID NO: 11). In order to obtain a stable IT, it is essential to ensure that during renaturation $V_H$ is positioned near $V_L$. This was achieved by mutating a single key residue in each chain to cysteine, for the stabilizing disulfide bond to form. On the basis of predictions using molecular modeling and empirical data with other dsFv-recombinant ITs, we chose one amino acid in each chain to mutate to cysteine {Reiter, 1996}. These are residues 44 in the framework region 2 (FR2) of $V_H$ and 100 in the FR4 of $V_L$ (according to the Kabat numbering). Thus, we prepared an Fv that contains both a peptide linker and a disulfide bond generated by cysteine residues that replace Ser44 of $V_H$ and Gly100 of $V_L$. The D2C7 (scdsFv) PCR fragment was then fused to DNA for domains II and III of *Pseudomonas* exotoxin A. The version of *Pseudomonas* exotoxin A used here, PE38KDEL, has a modified C terminus which increases its intracellular retention, in turn enhancing its cytotoxicity. The D2C7-(scdsFv)-PE38KDEL (FIG. 2) was expressed in *E. coli* under the control of T7 promoter and harvested as inclusion bodies. The IT was refolded and purified as described in "Materials and Methods."

Example 4

Antigen Binding Characteristic of D2C7-(scdsFv)-PE38KDEL Antibody.

Figure 3A:
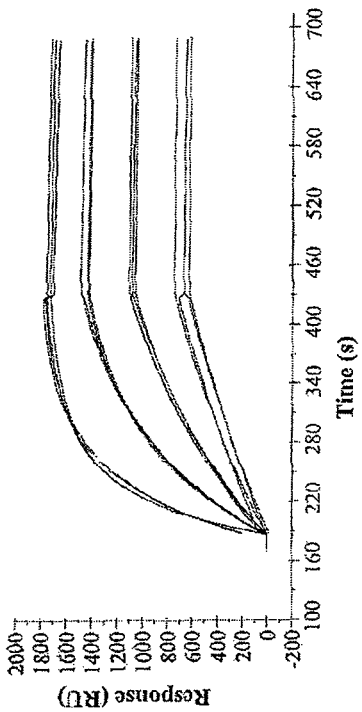
FIG. 3A-3B. Biacore analysis of D2C7 (scdsFv)-PE38KDEL. Binding kinetics and affinity constants of D2C7 (scdsFv)-PE38KDEL for EGFRwt (FIG. 3A) and EGFRvIII (FIG. 3B) were determined by surface plasmon resonance against bacterially expressed recombinant EGFRwt or EGFRvIII extracellular domain proteins. The association and dissociation rates from the sensogram were KA=$6.3\times10^8$ $M^{-1}$ and KD=$1.6\times10^{-9}$ M against EGFRwt and KA=$7.8\times10^8$ $M^{-1}$ and KD=$1.3\times10^{-9}$ M against EGFRvIII.
Figure 3B:
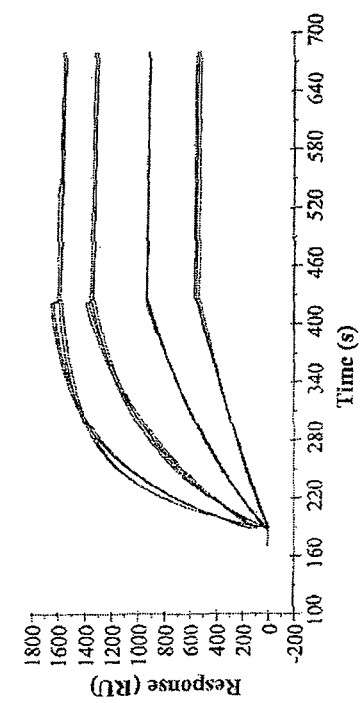

The antigen-binding capability of the D2C7-(scdsFv)-PE38KDEL IT was assessed by surface plasmon resonance (Biacore). The purified D2C7-(scdsFv)-PE38KDEL IT was applied to sensor chips that were coated with either purified recombinant EGFRwt (FIG. 3A) or EGFRvIII (FIG. 3B) ECD proteins. The D2C7-(scdsFv)-PE38KDEL IT bound to both the EGFRwt- and the EGFRvIII-ECD-protein-coated chips. Values of the on rates and off rates were determined for four different concentrations of the IT. The association and dissociation constants of D2C7-(scdsFv)-PE38KDEL IT on the EGFRwt- and EGFRvIII-coated chips were $K_A=6.3\times10^8$ $M^{-1}$ and $K_D=1.6\times10^{-9}M$ and $K=7.8\times10^8$ $M^{-1}$ and $K_d=1.3\times10^{-9}$ M, respectively. Thus, the cloned D2C7-(scdsFv)-PE38KDEL IT binds with similar kinetics to both the wild-type and the mutant EGFR proteins.

Figure 4A:
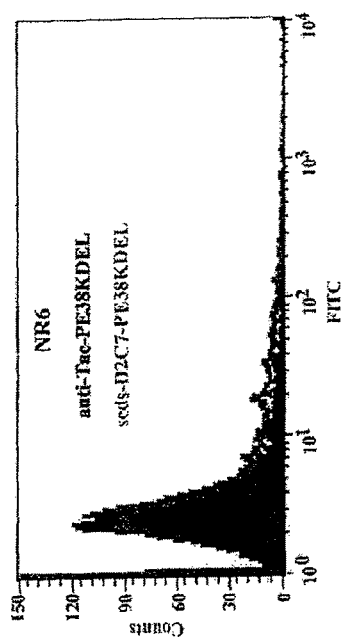
FIG. 4A-4C. Flow cytometric analysis of D2C7 (scdsFv)-PE38KDEL immunotoxin to determine reactivity of the D2C7 IT.
Figure 4B:
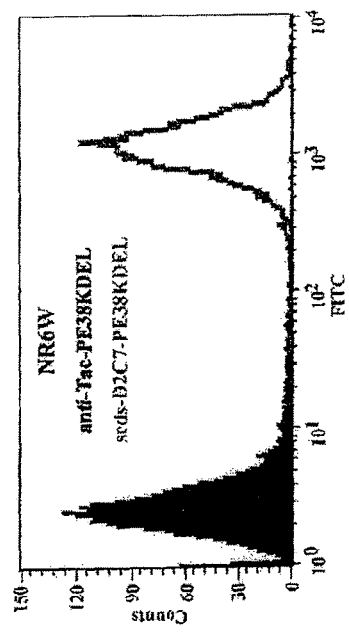
Figure 4C:
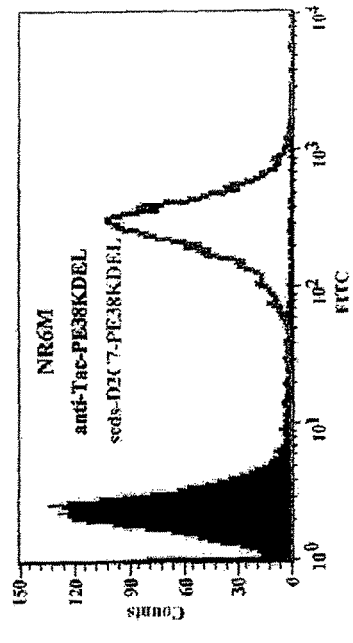
Figure 7A:
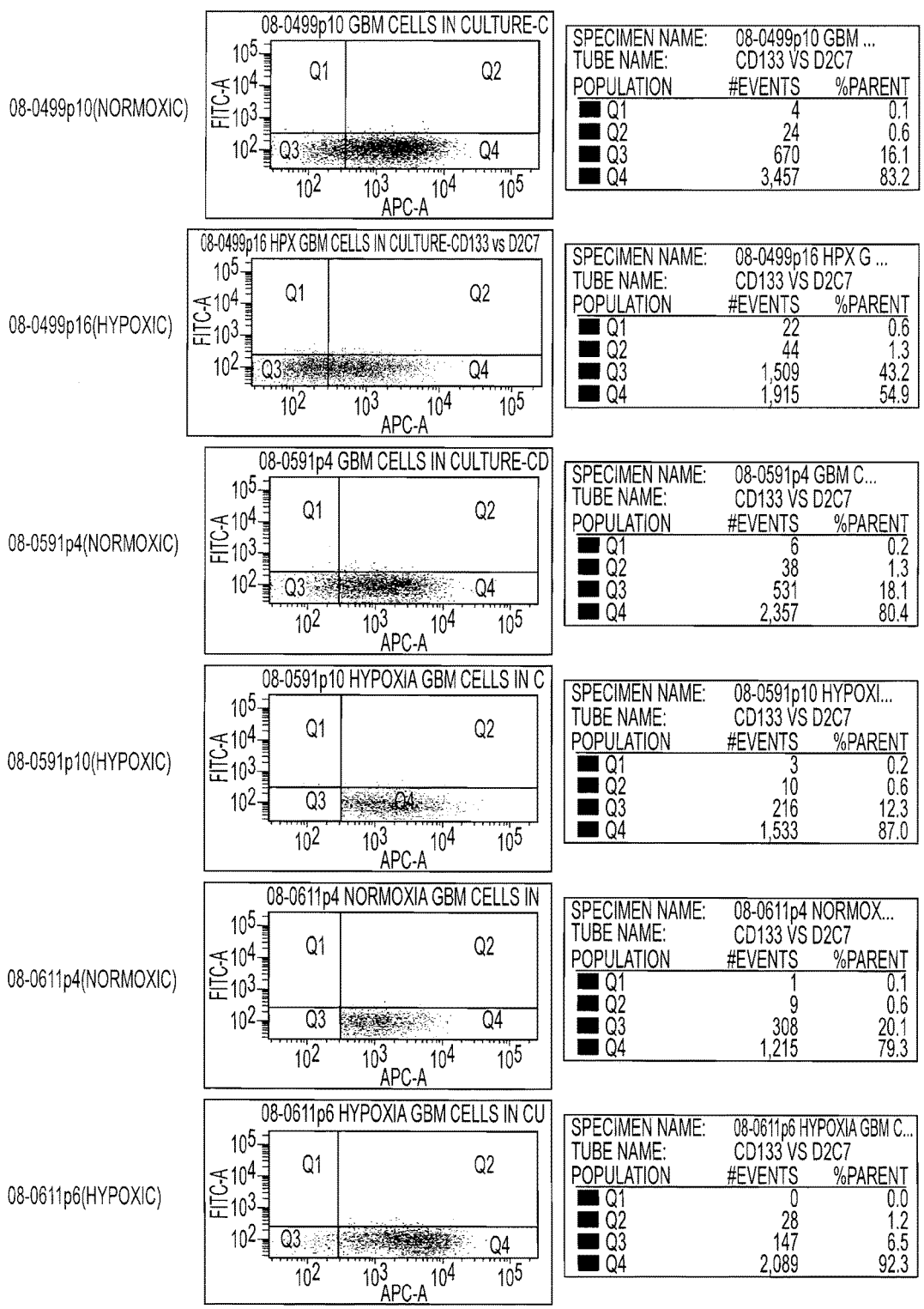
FIG. 7A-7W. Expression of tumor antigens and CD133 analyzed by flow cytometry.
Figure 7C:
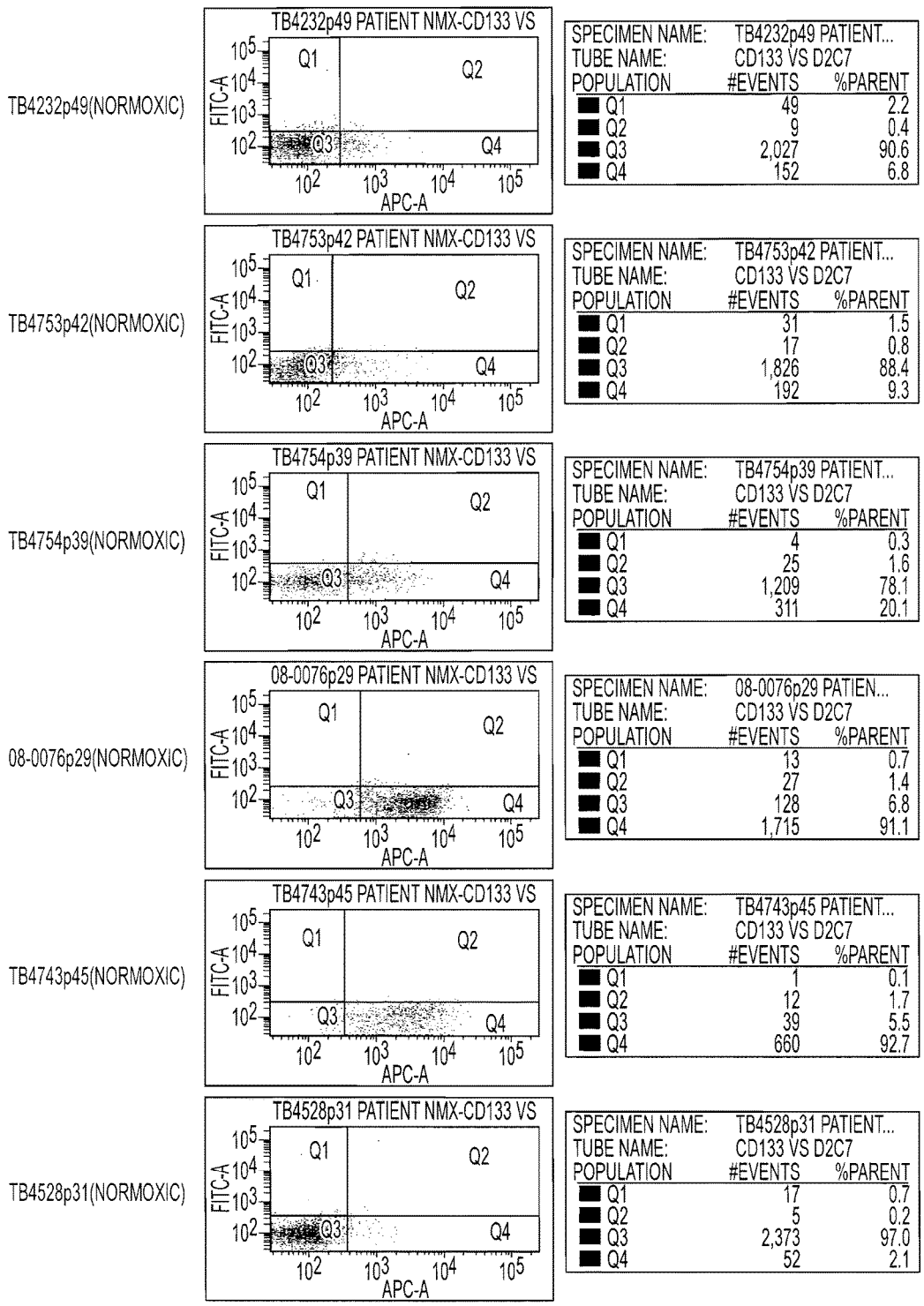
Figure 7D:
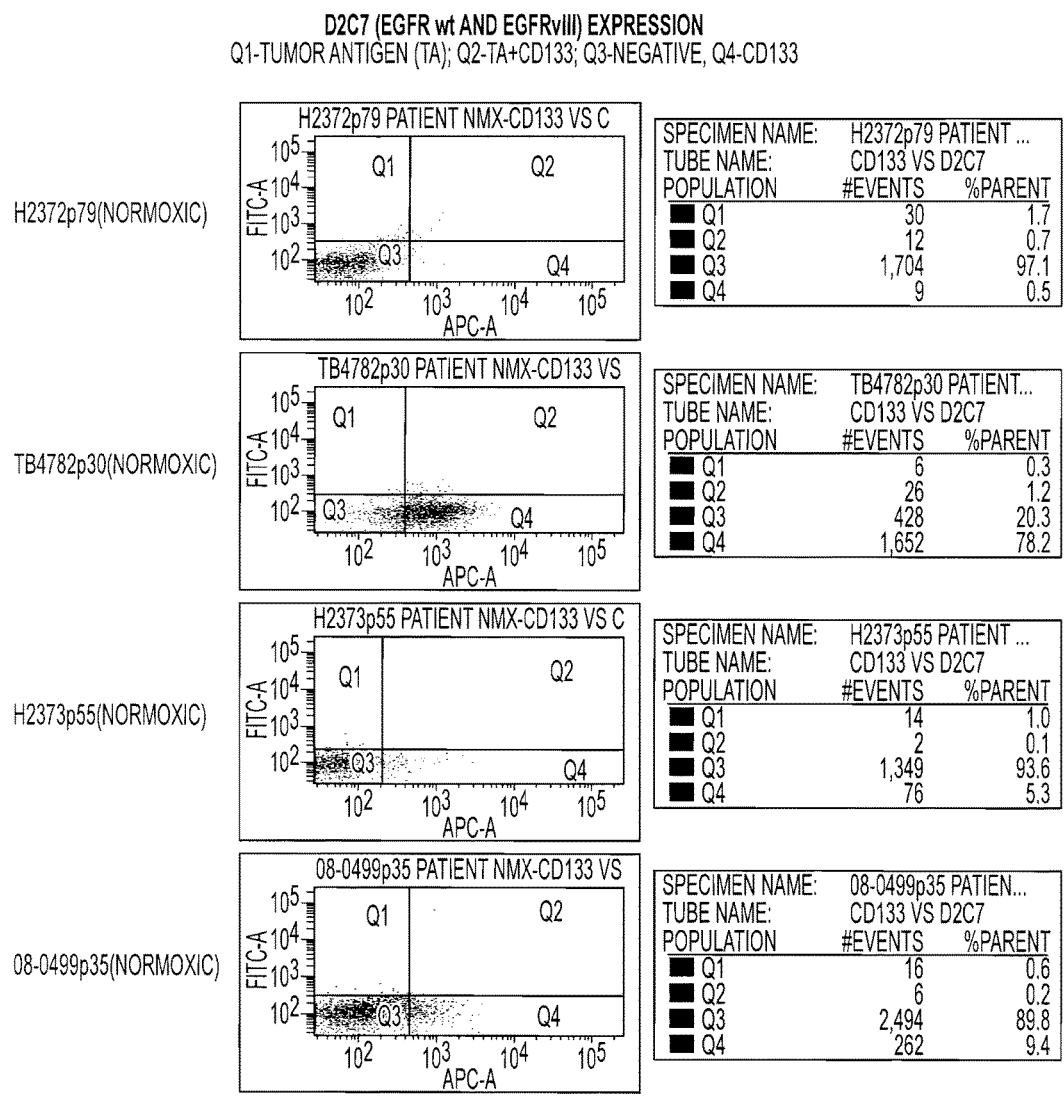
Figure 7E:
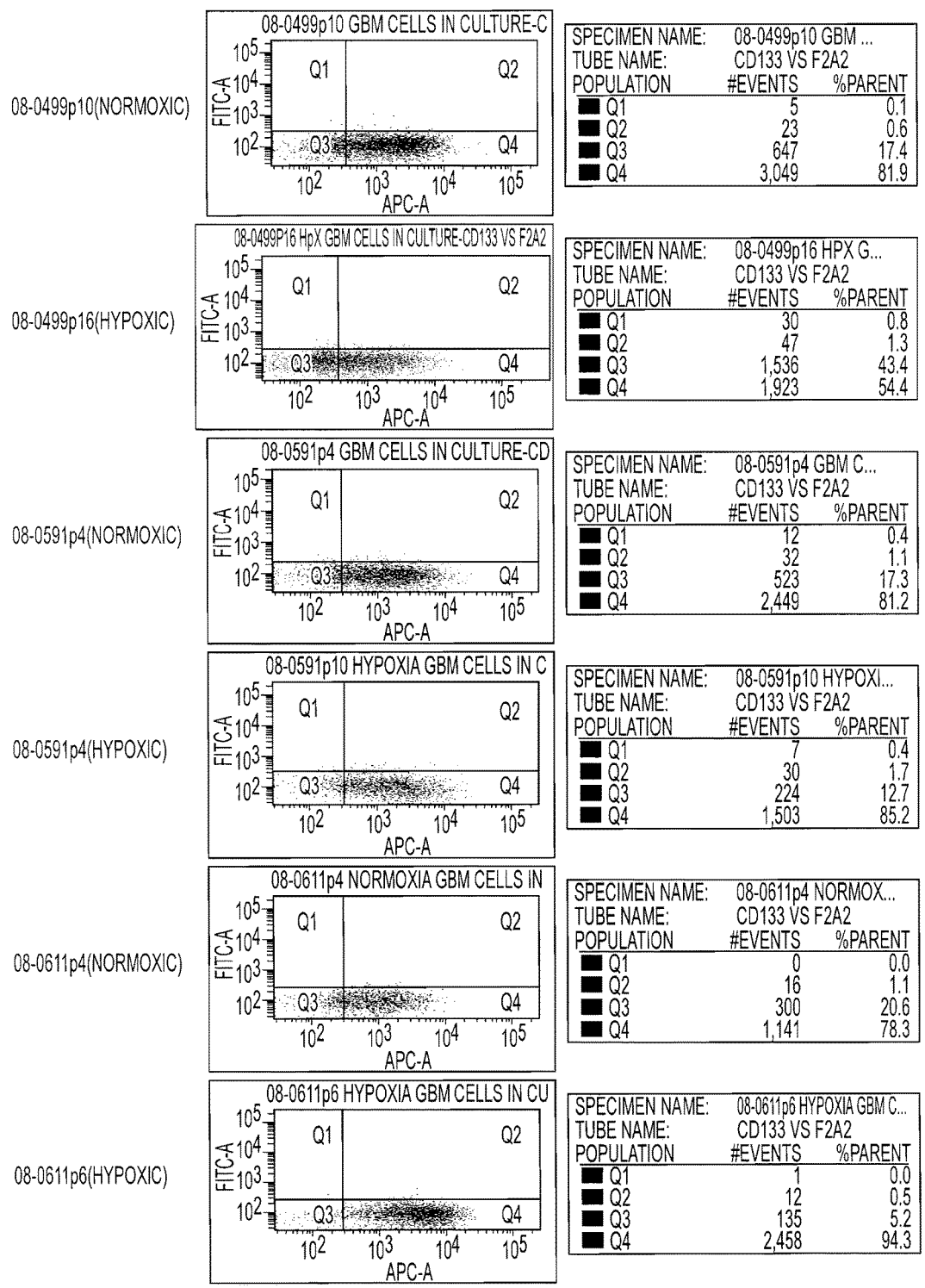
Figure 7G:
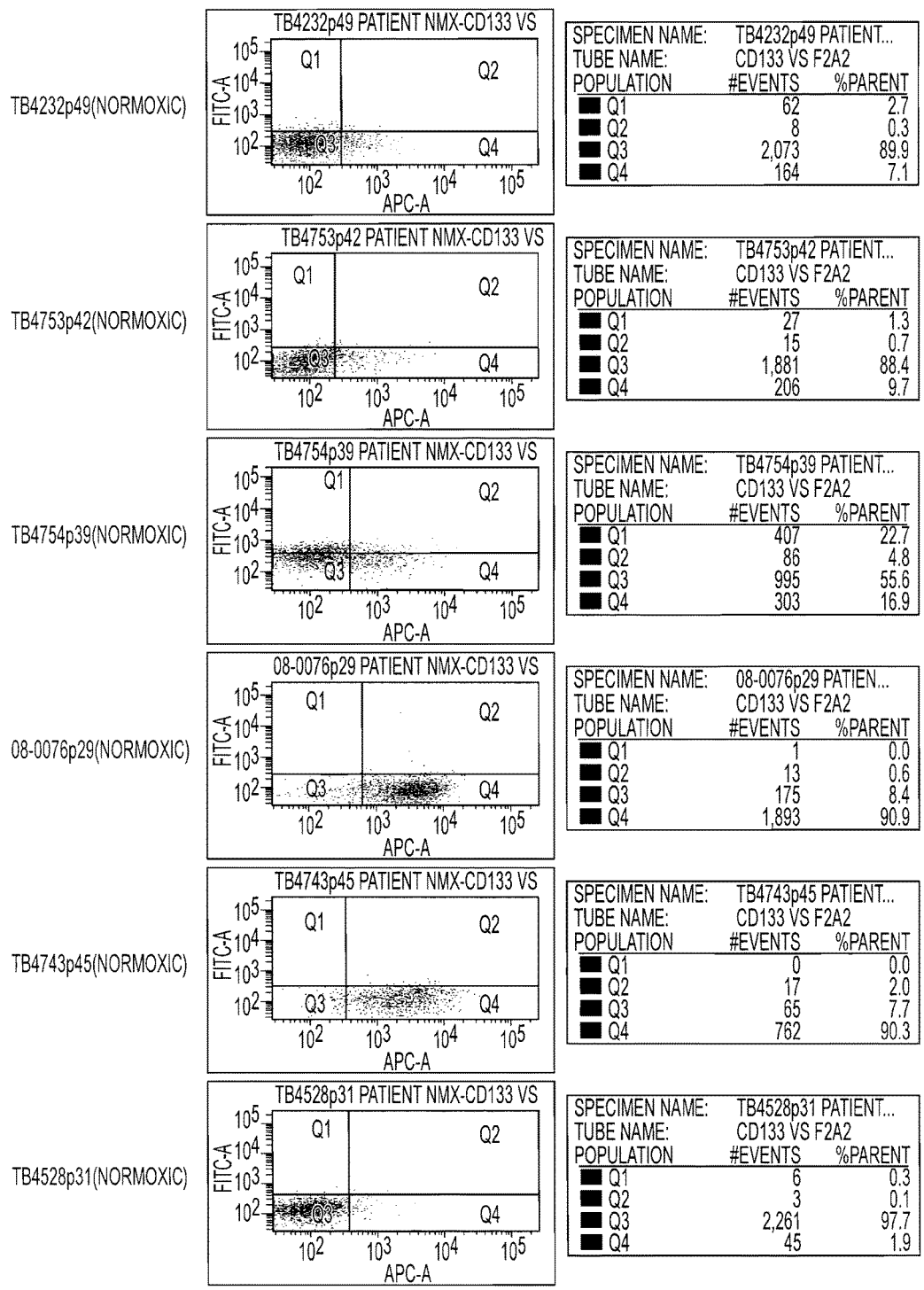
Figure 7I:
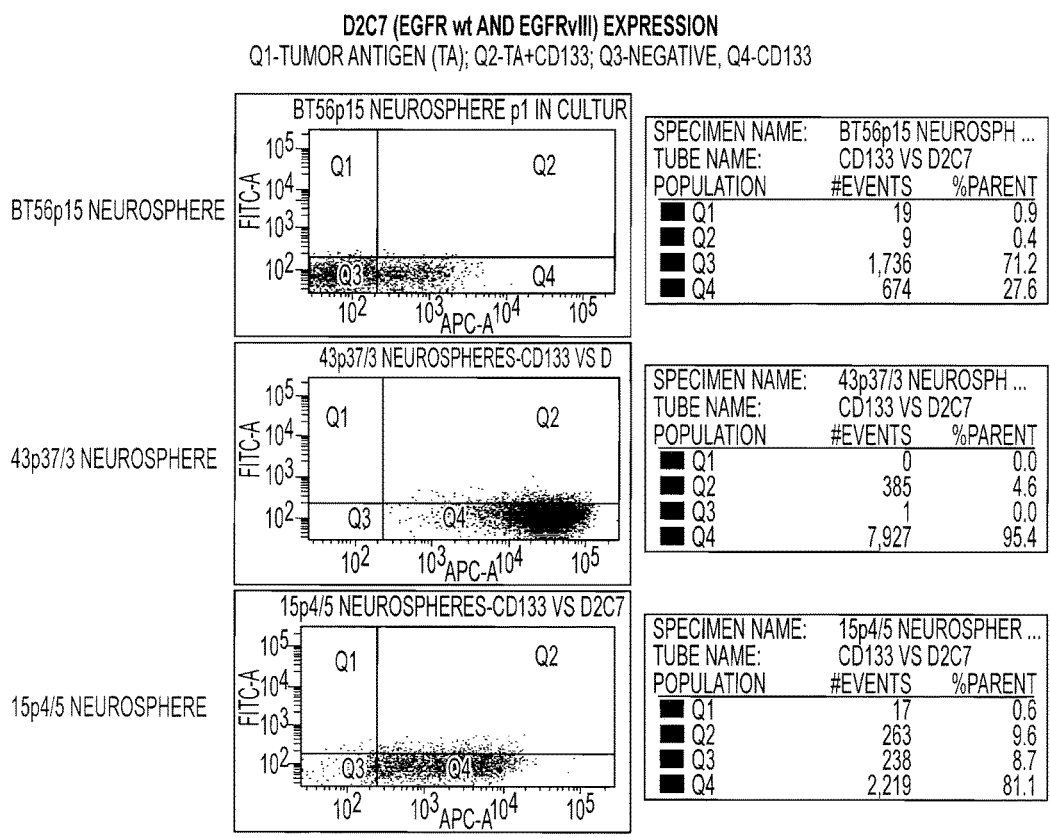
Figure 7J:
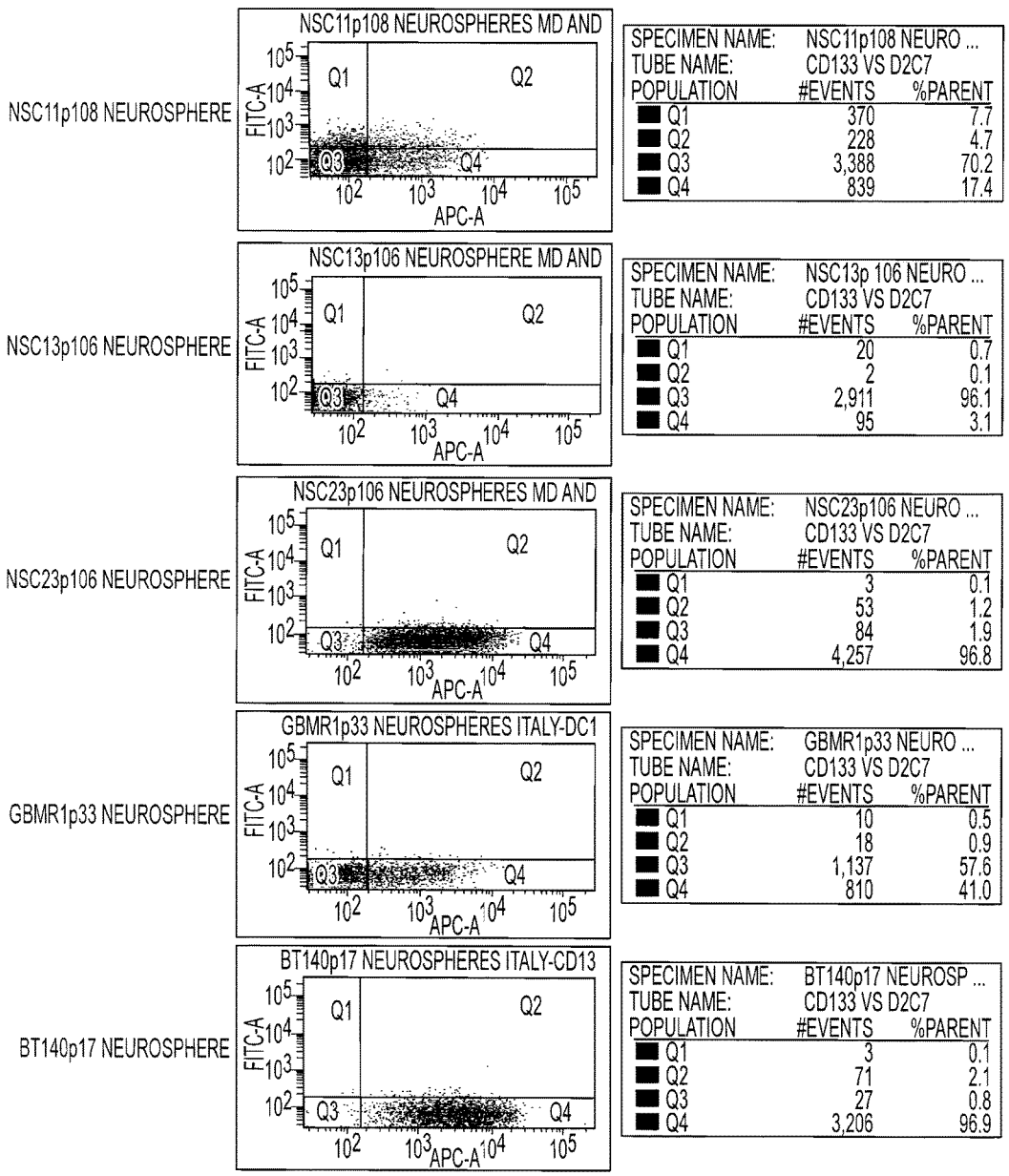
Figure 7L:
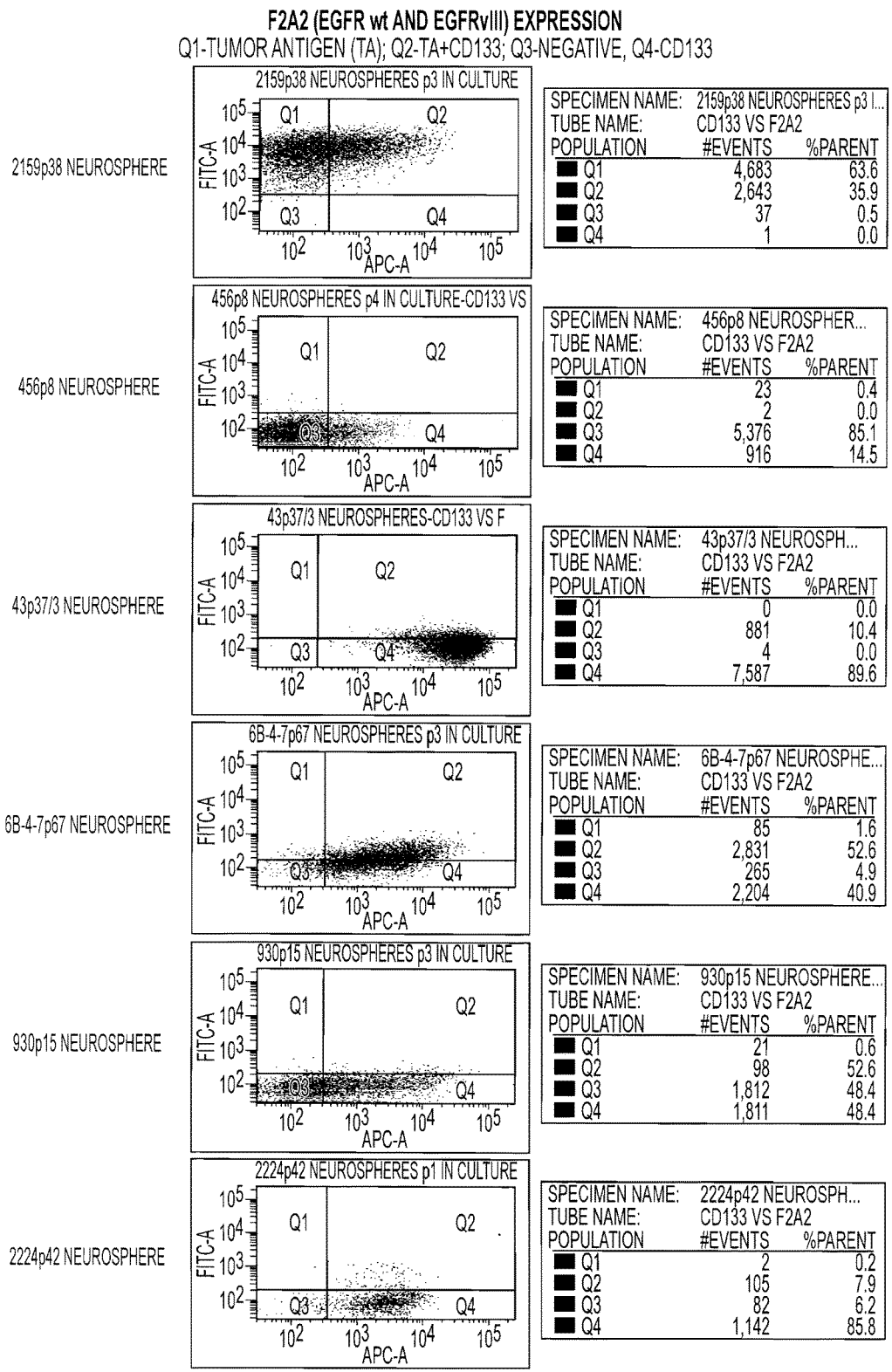
Figure 7M:
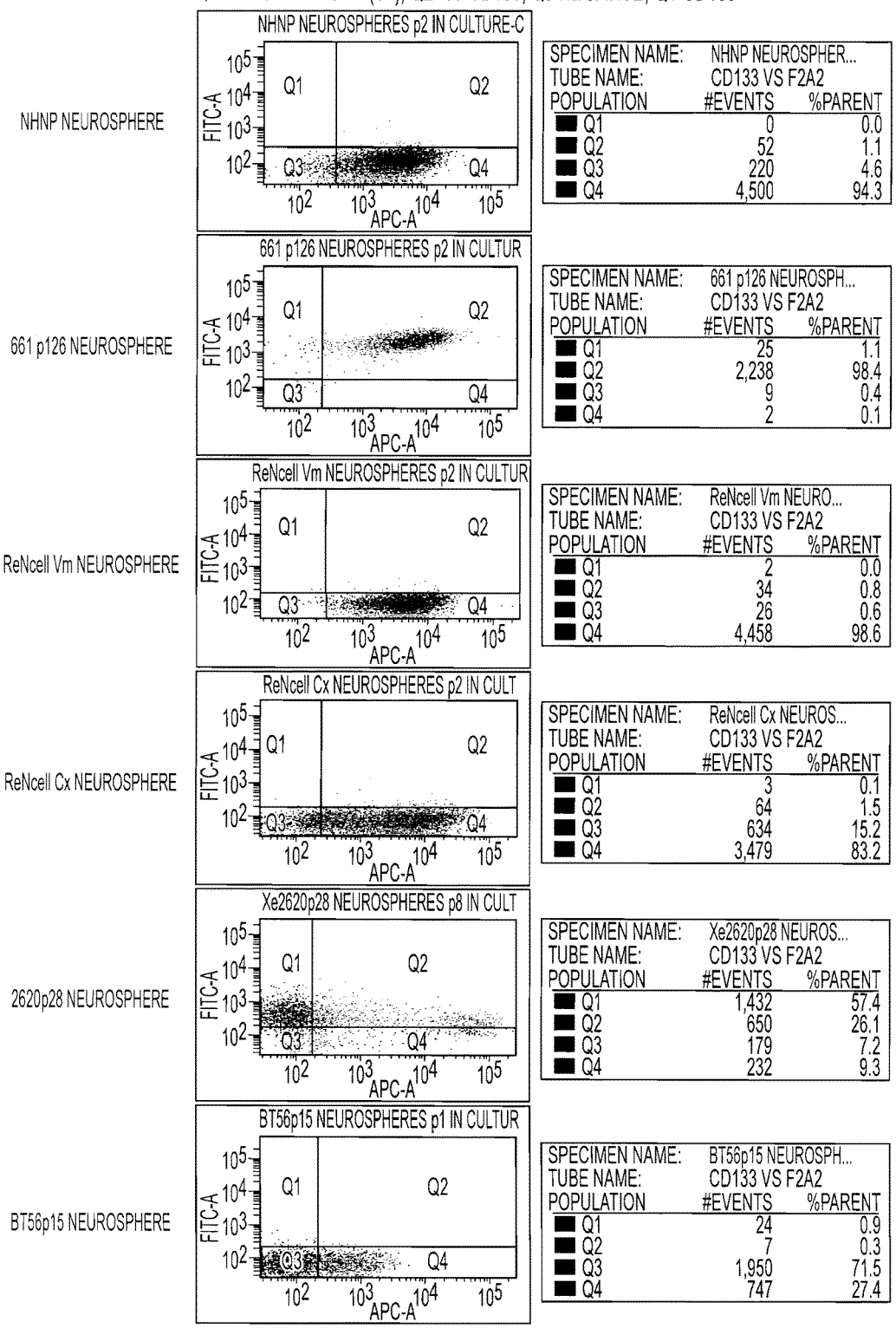
Figure 7N:
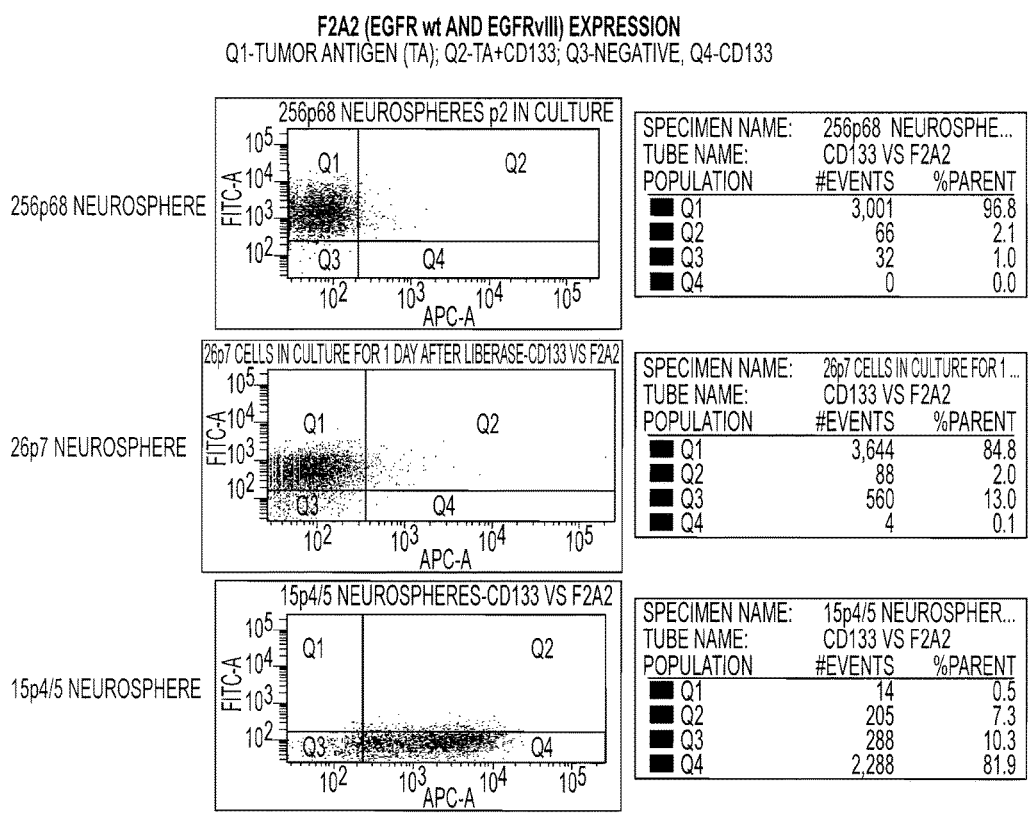
Figure 7O:
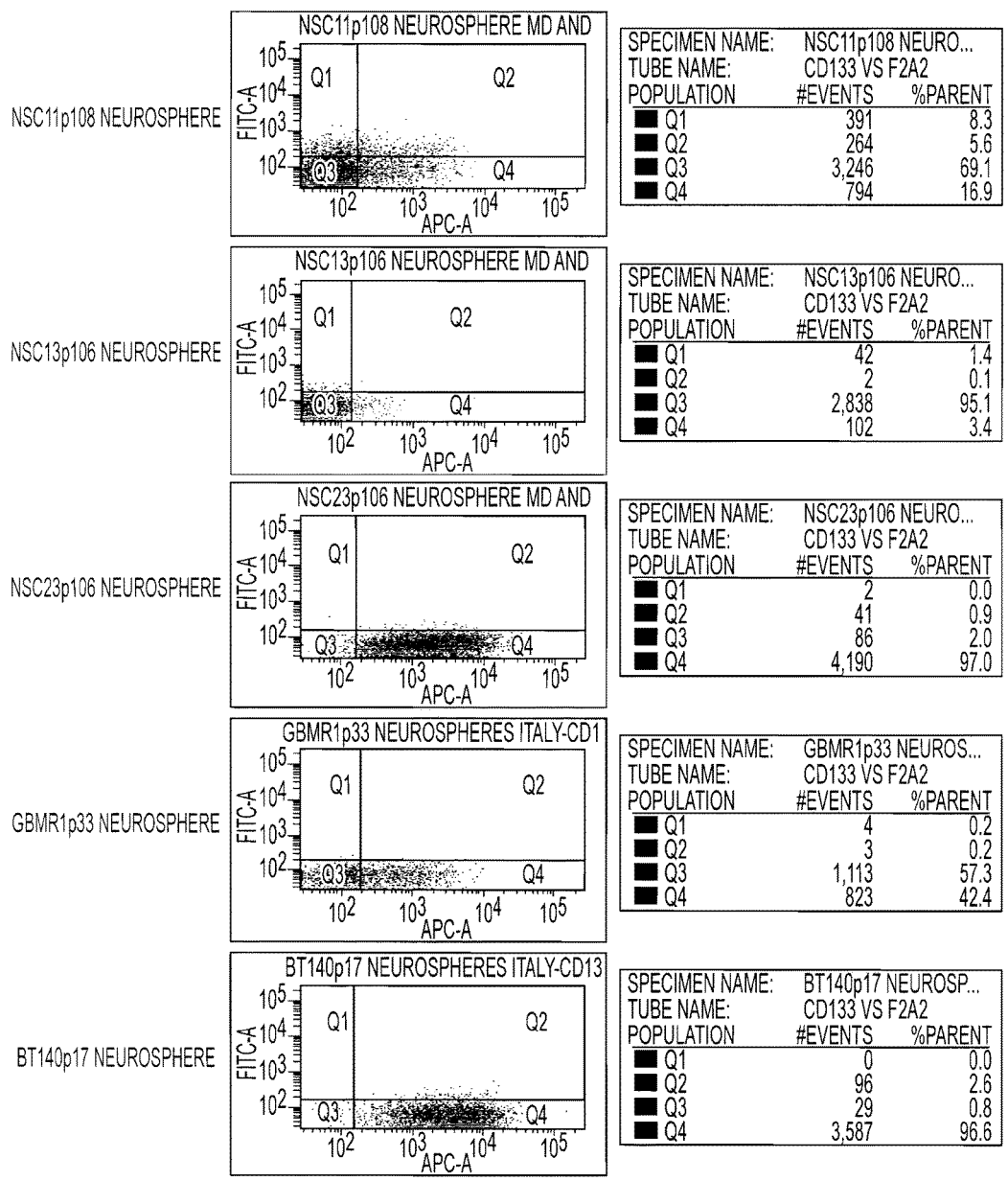
Figure 7S:
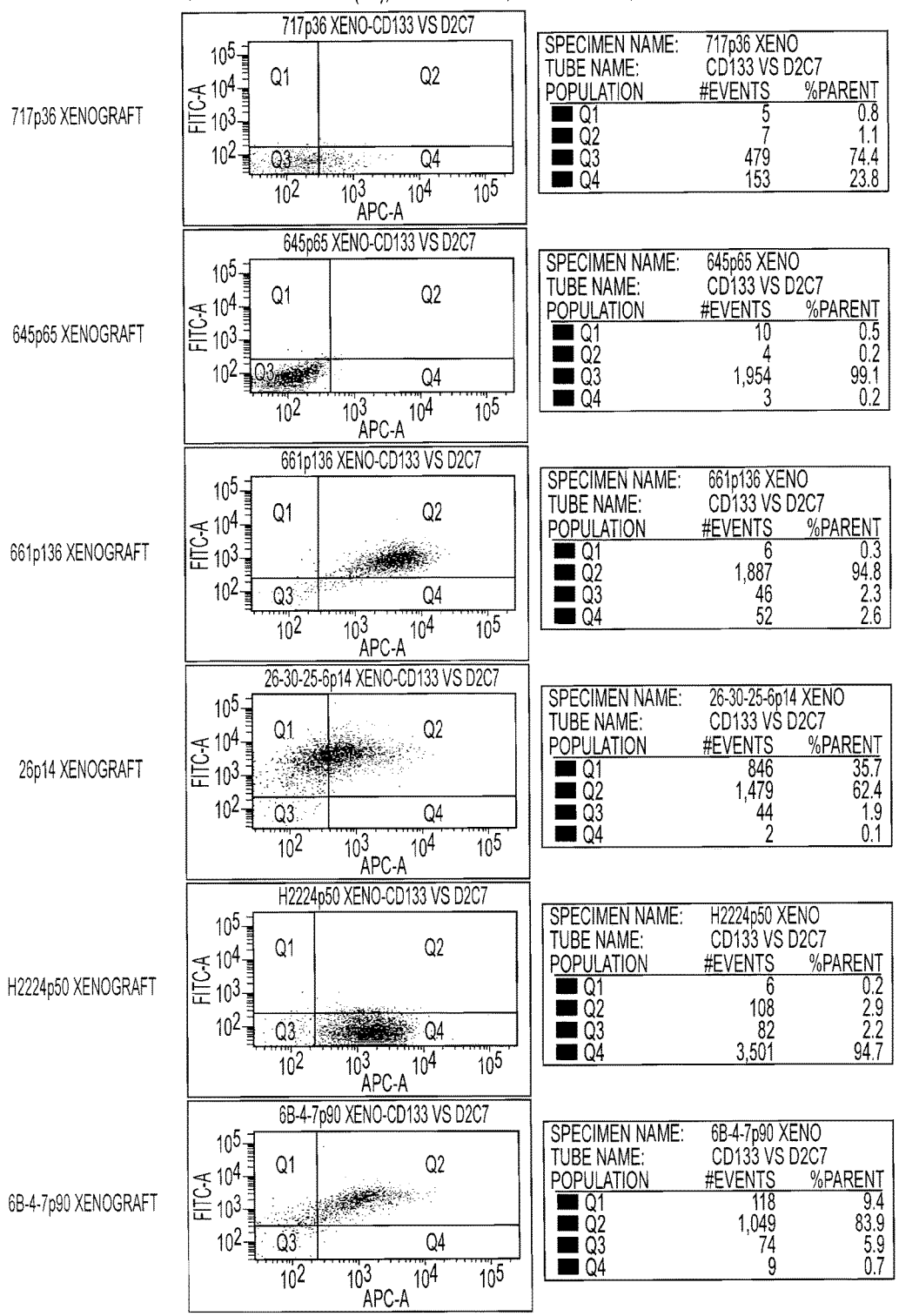

To determine whether the D2C7-(scdsFv)-PE38KDEL IT is able to bind to native EGFRwt and EGFRvIII proteins, indirect flow cytometric analysis was performed as shown in FIG. 4. FACS analysis revealed that the D2C7-(scdsFv)-PE38KDEL IT is able to bind to both the EGFRwt-expressing NR6W cells (FIG. 4B) and the EGFRvIII-expressing NR6M cells (FIG. 4C). The parental NR6 cells (FIG. 4A) were used as negative control, which confirmed the binding specificity of this toxin. These results demonstrate that the D2C7-(scdsFv)-PE38KDEL IT is able to bind both to the purified EGFRwt and the EGFRvIII proteins on a chip and to the native protein molecules expressed on the surface of transfected cells.

Example 5

Cytotoxicity of D2C7-(scdsFv)-PE38KDEL IT on Transfected Cells and Cancer Cell Lines.

We next examined the effects of D2C7-(scdsFv)-PE38KDEL IT on EGFRwt- or EGFRvIII-transfected NR6W and NR6M mouse cell lines, respectively. The ability of the D2C7-(scdsFv)-PE38KDEL IT to inhibit protein synthesis was used as a measure of its cytotoxic effect. The cytotoxicity of D2C7-(scdsFv)-PE38KDEL IT was compared to that of a known EGFRvIII-specific IT, MR1-1-(scdsFv)-PE38KDEL (MR1-1) {Beers, 2000} and that of the parental D2C7-PE38 IT, which lacks the disulfide-stabilized linkage and the endoplasmic reticulum retention signal, KDEL. We initially evaluated the cytotoxicity of the various ITs to the EGFRwt-expressing NR6W cells. The $IC_{50}$ of D2C7-(scdsFv)-PE38KDEL IT on NR6W cells (FIG. 5B) was more than 100-fold lower than that of the MR1-1 IT. Even on the NR6M cells (FIG. 5C), a well-established model for MR1-1 cytotoxicity {Beers, 2000}, D2C7-(scdsFv)-PE38KDEL IT had a 1.4-fold lower $IC_{50}$ value than that of MR-1-1 IT. The $IC_{50}$ of D2C7-(scdsFv)-PE38KDEL IT was approximately 7-fold lower than that of the parental D2C7-PE38 IT, against both NR6W and NR6M cells (FIGS. 5B and 5C). All of the ITs exhibited no cytotoxicity against the parental NR6 cells (FIG. 5A). The cytotoxic effects of D2C7-(scdsFv)-PE38KDEL IT were also tested on various EGFRwt- and EGFRvIII-positive human cancer cell lines. The A431P epidermoid carcinoma cell line overexpresses the wild-type EGFR protein, and the three glioblastoma cell lines D2159MG, D270MG and D256MG express both the EGFRwt and EGFRvIII proteins. As shown in Table 1, the D2C7-(scdsFv)-PE38KDEL IT was more effective than the parental IT, D2C7-PE38, and the EGFRvIII-targeted IT, MR1-1, in killing all the human cancer cell lines tested.

TABLE 1

Cytotoxicity of D2C7 and MR1-1 immunotoxins toward various cell lines

| Cell Line | Cancer type | D2C7-PE38 $IC_{50}$ ng/ml | D2C7-(scdsFv)-PE38KDEL $IC_{50}$ ng/ml | MR1-1-(scdsFv)-PE38KDEL $IC_{50}$ ng/ml |
|---|---|---|---|---|
| A431 | Epidermoid | 1.0 | 0.170 | 8.0 |
| D2159MG | Glioblastoma | 1.8 | 0.360 | 0.800 |
| D270MG | Glioblastoma | 1.8 | 0.360 | 0.580 |
| D256MG | Glioblastoma | 5.1 | 0.520 | 1.9 |

NOTE:
All the cell lines are of human origin.
Cytotoxicity data are given as $IC_{50}$ value, the concentration of immunotoxin that causes a 50% inhibition of protein synthesis after a 20-h incubation with immunotoxin.

Example 6

Nonspecific Toxicity of D2C7-(scdsFv)-PE38KDEL IT in Mice.

The nonspecific toxicity of D2C7-(scdsFv)-PE38KDEL IT was evaluated in BALB/C mice. Groups of 10 mice were given single i.p. injections of escalating doses of the IT. The mice were monitored for weight loss, signs of distress, or death for 14 days postinjection. The mortality data is shown in Table 2. Almost all of the deaths occurred within 72 h after treatment. We calculated the $LD_{10}$ of D2C7-(scdsFv)-PE38KDEL IT to be approximately 0.3125 mg/kg. The observed toxicity in mice is due to nonspecific uptake of the IT by the liver.

TABLE 2

Toxicity of D2C7-(scdsFv)-PE38KDEL immunotoxin administered to BALB/C mice

| Dose (mg/kg) | Mortality |
|---|---|
| 0.25 | 0/10 |
| 0.5 | 4/10 |
| 0.75 | 8/10 |
| 1.0 | 9/10 |
| 1.25 | 10/10 |

NOTE:
Groups of 10 BALB/C mice were injected i.p. with 200 μl of escalating doses of the IT diluted in 0.2% PBS-HSA.
Animals were observed for 14 days.
Mortality is expressed as number of dead mice/total number of animals in treatment group.

Example 7

Anti-Tumor Activity of D2C7-(scdsFv)-PE38KDEL IT In Vivo.

To evaluate the anti-tumor activity of the ITs, animals bearing A431 tumors were treated with three doses of either D2C7-(scdsFv)-PE38KDEL or MR1-1 (MR1-1 scFv binds with a lower affinity to the wild-type EGFR, unpublished data) at 0.3 mg/kg concentration. Relative to the control group, the D2C7-(scdsFv)-PE38KDEL-treated mice showed statistically significant growth delay, where T–C was 22 days ($p<0.001$) (FIG. 6A and Table 3). In contrast, the growth delay in the MR1-1 treated group was approximately 4 days ($p=0.01$) (FIG. 6A and Table 3). The A431 tumors regressed in 7 of 8 mice treated with D2C7-(scdsFv)-PE38KDEL, whereas no tumor regression was observed in the MR1-1-treated A431 group. In an in vivo xenograft model of NR6M tumors, both D2C7-(scdsFv)-PE38KDEL and MR1-1 elicited similar responses (FIG. 6B and Table 3).

In comparison to the control group, the D2C7-(scdsFv)-PE38KDEL-treated group and the MR1-1-treated group had a growth delay of 10 and 9 days, respectively, with a p value of <0.001 (FIG. 6B and Table 3). Tumor regression was seen in 10 of 10 mice in the D2C7-(scdsFv)-PE38KDEL-treated group, but only 6 of 10 mice in the MR1-1-treated group displayed tumor regression.

TABLE 3

In vivo anti-tumor activity of
D2C7-(scdsFv)-PE38KDEL and MR1-1-(scdsFv)-PE38KDEL

| Tumor | Control | D2C7-(scdsFv)-PE38KDEL | MR1-1-(scdsFv)-PE38KDEL |
|---|---|---|---|
| A431 | | | |
| T-C (days) | | 22.177 | 3.6875 |
| P | | <0.001 | 0.01 |
| Regressions | 0/8 | 7/8 | 0/9 |
| NR6M | | | |
| T-C (days) | | 10.6565 | 9.1835 |
| P | | <0.001 | <0.001 |
| Regressions | 0/10 | 10/10 | 6/10 |

NOTE:
Groups of 8 to 10 nude mice bearing A431 or NR6M tumors were treated with 0.3 mg/kg of the IT diluted in 0.2% PBS-HSA.
T-C denotes the delay in tumor growth in mice treated with IT as compared with control mice.
Tumor regression was defined as a decrease in tumor volume over two successive measurements.

Example 8

In this study, we have focused on the in vitro and in vivo characterization of a dual-specificity (EGFRwt/EGFRvIII) IT, D2C7-(scdsFv)-PE38KDEL. The results from the in vitro cytotoxicity assays showed that D2C7-(scdsFv)-PE38KDEL is highly effective in killing a variety of EGFRwt- or EGFRvIII-expressing human tumor cell lines. In an animal model of EGFRwt tumors, when administered every other day for a total of three doses at a concentration of 0.3 mg/kg, the IT inhibited tumor growth, leading to a decrease in tumor volume. In addition, D2C7-(scdsFv)-PE38KDEL was also found to be as effective as that of an established, affinity-matured, EGFRvIII-targeted IT, MR1-1, in both in vitro and in vivo assays. To the best of our knowledge, this is the first report demonstrating that a dually specific IT can target both the wild-type EGFR and the mutant EGFRvIII.

Different versions of the D2C7 IT were constructed that vastly improved its efficacy. The parental D2C7-PE38 IT had only a 15-amino-acid peptide linker between $V_H$ and $V_L$. The subsequent version of the IT had both a 15-amino-acid peptide linker and a disulfide linkage between $V_H$ and $V_L$ [D2C7-(scdsFv)-PE38]. The disulfide linkage helps the IT to fold better, in turn providing improved stability. The D2C7-(scdsFv)-PE38 IT showed a 2- to 4-fold decrease in $IC_{50}$ values compared to the parental D2C7-PE38 IT (data not shown). Further, when the endoplasmic reticulum retention signal KDEL was engineered into the final product [D2C7-(scdsFv)-PE38KDEL], it decreased the $IC_{50}$ values of the IT on all of the cell lines tested by an additional 2-fold. Thus, increasing the stabilization and adding an intracellular retention signal enhanced the efficiency of D2C7-(scdsFv)-PE38KDEL when compared with that of the parental D2C7-PE38 IT.

In the in vitro cytotoxicity assays with either the EGFRvIII-transfected NR6M cells or EGFRvIII-expressing GBM cells, D2C7-(scdsFv)-PE38KDEL outperformed MR1-1. The difference in $IC_{50}$ values between D2C7-(scdsFv)-PE38KDEL and MR1-1 was higher in the EGFRwt- and EGFRvIII-co-expressing GBM cells than in the EGFRvIII-expressing NR6M cells. The presence of both the wild-type and the mutant EGFR proteins on the GBM cells provides a higher concentration of targets on the cell surface for D2C7-(scdsFv)-PE38KDEL as opposed to a single target for MR1-1. Hence, on the cells that express both the EGFRwt and EGFRvIII proteins, D2C7-(scdsFv)-PE38KDEL exhibited better cytotoxicity than MR1-1. Also, a competition assay by Biacore analysis with EGFRvIII ECD protein revealed that D2C7-(scdsFv)-PE38KDEL and MR1-1 bind to different epitopes (data not shown). Thus, the availability of the epitopes on the cell surface for the ITs to bind might also play a role in the observed difference in cytotoxicity between D2C7-(scdsFv)-PE38KDEL and MR1-1.

Several anti-EGFR mAbs that have demonstrated antitumor activity against EGFR-expressing human tumor cells in mouse xenograft models and/or culture have been developed {Laskin, 2004}. Some of these anti-EGFR mAbs are in clinical trials for a variety of human cancers, including head and neck, colorectal, pancreatic, lung, renal cell or prostate carcinoma, or high-grade glioma {Boskovitz, 2004; Laskin, 2004}. Anti-EGFRwt mAbs EGFR1, H17E2, and mAb 425 were the first to be introduced in targeted radiotherapy trials that involved systemic injection of radiolabeled mAb in patients with malignant glioma {Brady, 1992; Epenetos, 1985; Kalofonos, 1989}. The anti-EGFR mAbs that are currently in Phase II trials for patients with high-grade glioma include $^{125}$I-labeled mAb 425 in combination with surgery, radiation therapy and chemotherapy (Protocol IDs: 12555, NCT00589706), which has already demonstrated an increase in median survival {Quang, 2004}. Further, a recombinant EGFR ligand (transforming growth factor-a) *Pseudomonas* exotoxin fusion protein (TP-38) has also been tested in Phase I clinical trials for treating malignant gliomas {Sampson, 2008}.

Because of the truly tumor-specific nature of EGFRvIII, both polyclonal antibodies and mAbs directed against this mutant form of EGFR have been developed {Humphrey, 1990; Wikstrand, 1995}. The development of mAbs and single-chain fragment antibody constructs specific for the mutant EGFRvIII, including L8A4, Y10, P14, X32, MR1, MR1-1, and 14E1, has been well described {Beers, 2000; Kuan, 1999; Kuan, 2000; Reist, 1995; Schmidt, 1999; Wikstrand, 1995; Wikstrand, 1997}. Among the various antibody constructs, the one with enormous potential is the MR1 single-chain antibody fragment, as well as its affinity-matured derivative MR1-1 {Beers, 2000; Kuan, 1999; Kuan, 2000}. MR1-1, which differs from the parental MR1 by three amino acid residues (one in $V_{LCDR3}$ [F92W] and two in $V_{HCDR3}$ [S98P, T99Y]), has a 15-fold greater $K_D$ (1.5× $10^{-9}$ M) for the extracellular domain of EGFRvIII than does MR1 {Kuan, 2000}. A Phase I clinical study with the MR1-1 IT is currently underway for the treatment of patients with EGFRvIII-overexpressing GBM tumors. Due to the recurrent nature of malignant gliomas, as well as the diversity of antigens populating the glioma cell surface, innovative therapies are needed.

The EGFRvIII mutation occurs in 52% of all human GBMs and is co-expressed in 50% to 60% of tumors that have EGFRwt amplification {Frederick, 2000; Wikstrand, 1995}. Thus, it would be advantageous to have antibodies that could target both EGFRwt and EGFRvIII antigens for GBM therapy. This could be achieved by co-targeting these two antigens with a bispecific scFv antibody, an scFv antibody that has dual specificity. This could promote increased targeting of the tumor over antibodies specific for a single antigen. No bispecific scFv that can target both EGFRwt and EGFRvIII has been reported, although reports have been published describing two mAbs, mAb 528 and mAb 806, with dual specificity for the wild-type and mutant EGFR proteins expressed on different cell lines. The mAb 528 is an IgG2a antibody that was raised against EGFR by using the epidermoid carcinoma cell line A431 {Masui, 1984}. This antibody binds both the EGFRwt expressed on A431 cells and EGFRvIII expressed on U87MG A2-7 {Perera, 2005}. Monoclonal antibody 528 competes with EGF binding to the receptor and inhibits the growth of EGFR-expressing cells both in vitro and in vivo {Masui, 1984}. The IgG2b mAb 806 is an EGFR-specific antibody that was raised in mice immunized with NR6 cells transfected with EGFRvIII {Johns, 2002}. The mAb 806 binds EGFRvIII with high affinity and EGFRwt at a low percentage (10%) on A431 cells {Johns, 2002}. A humanized form of the mAb 806 (ch806) was used in Phase I clinical trials for patients with diverse tumor types expressing EGFR {Scott, 2007}. Combination therapy with the mAbs 528 and 806 was performed with xenografts expressing EGFRwt or EGFRvIII. A significant decrease in tumor volume was observed when the mAbs were administered in combination {Perera, 2005}. In our in vivo models, the tumor growth inhibition by D2C7-(scdsFv)-PE38KDEL at 3 doses was comparable to the response observed with the mAbs 528 and 806 together, for a total of 6 doses. Hence, the dual-specificity IT is likely more efficacious than the combined mAb treatment. Moreover, treating brain tumors that co-express EGFRwt and EGFRvIII with D2C7-(scdsFv)-PE38KDEL IT will address the concern that expression of EGFRvIII may cause resistance to EGFR antibody therapy. Thus, a single antibody with specificity against two different tumor antigens eliminates the necessity for multiple therapeutics to treat tumor.

In conclusion, we have created a dual specific-scFv molecule that is capable of mediating selective in vitro and in vivo tumor targeting. Further, we believe this to be the first significant evidence of enhanced tumor targeting with high selectivity and specificity by an antibody specific for two tumor-associated antigens. Taken together, our results suggest that the bispecific antibody D2C7-(scdsFv)-PE38KDEL may be efficacious in vivo against brain tumors.

REFERENCES

The disclosure of each reference cited is expressly incorporated herein.
1. Louis D N, Gusella J F. A tiger behind many doors: multiple genetic pathways to malignant glioma. Trends Genet 1995; 11: 412-5.
2. Walker M D, Alexander E, Jr., Hunt W E, et al. Evaluation of BCNU and/or radiotherapy in the treatment of anaplastic gliomas. A cooperative clinical trial. Journal of neurosurgery 1978; 49: 333-43.
3. Levin V A, Wara W M, Davis R L, et al. Phase III comparison of BCNU and the combination of procarbazine, CCNU, and vincristine administered after radiotherapy with hydroxyurea for malignant gliomas. Journal of neurosurgery 1985; 63: 218-23.
4. Stupp R, Hegi M E, Gilbert M R, Chakravarti A. Chemoradiotherapy in malignant glioma: standard of care and future directions. J Clin Oncol 2007; 25: 4127-36.
5. Boskovitz A, Wikstrand C J, Kuan C T, Zalutsky M R, Reardon D A, Bigner D D. Monoclonal antibodies for brain tumour treatment. Expert opinion on biological therapy 2004; 4: 1453-71.
6. Archer G E, Sampson J H, Lorimer I A, et al. Regional treatment of epidermal growth factor receptor vIII-expressing neoplastic meningitis with a single-chain immunotoxin, MR-1. Clin Cancer Res 1999; 5: 2646-52.
7. Pastan I H, Archer G E, McLendon R E, et al. Intrathecal administration of single-chain immunotoxin, LMB-7 [B3 (Fv)-PE38], produces cures of carcinomatous meningitis in a rat model. Proceedings of the National Academy of Sciences of the United States of America 1995; 92: 2765-9.
8. Ushiro H, Cohen S. Identification of phosphotyrosine as a product of epidermal growth factor-activated protein kinase in A-431 cell membranes. The Journal of biological chemistry 1980; 255: 8363-5.
9. Klijn J G, Berns P M, Schmitz P I, Foekens J A. The clinical significance of epidermal growth factor receptor (EGF-R) in human breast cancer: a review on 5232 patients. Endocrine reviews 1992; 13: 3-17.
10. Osaki A, Toi M, Yamada H, Kawami H, Kuroi K, Toge T. Prognostic significance of co-expression of c-erbB-2 oncoprotein and epidermal growth factor receptor in breast cancer patients. American journal of surgery 1992; 164: 323-6.
11. Pavelic K, Banjac Z, Pavelic J, Spaventi S. Evidence for a role of EGF receptor in the progression of human lung carcinoma. Anticancer research 1993; 13: 1133-7.
12. Rubin Grandis J, Melhem M F, Barnes E L, Tweardy D J. Quantitative immunohistochemical analysis of transforming growth factor-alpha and epidermal growth factor receptor in patients with squamous cell carcinoma of the head and neck. Cancer 1996; 78: 128492.
13. Fox S B, Persad R A, Coleman N, Day C A, Silcocks P B, Collins C C. Prognostic value of c-erbB-2 and epidermal growth factor receptor in stage A1 (T1a) prostatic adenocarcinoma. British journal of urology 1994; 74: 214-20.
14. Chow N H, Chan S H, Tzai T S, Ho C L, Liu H S. Expression profiles of ErbB family receptors and prognosis in primary transitional cell carcinoma of the urinary bladder. Clin Cancer Res 2001; 7: 1957-62.
15. Yasui W, Sumiyoshi H, Hata J, et al. Expression of epidermal growth factor receptor in human gastric and colonic carcinomas. Cancer research 1988; 48: 137-41.
16. Bartlett J M, Langdon S P, Simpson B J, et al. The prognostic value of epidermal growth factor receptor mRNA expression in primary ovarian cancer. British journal of cancer 1996; 73: 301-6.
17. Arita N, Hayakawa T, Izumoto S, et al. Epidermal growth factor receptor in human glioma. Journal of neurosurgery 1989; 70: 916-9.
18. Libermann T A, Razon N, Bartal A D, Yarden Y, Schlessinger J, Soreq H. Expression of epidermal growth factor receptors in human brain tumors. Cancer research 1984; 44: 753-60.
19. Fuller G N, Bigner S H. Amplified cellular oncogenes in neoplasms of the human central nervous system. Mutation research 1992; 276: 299-306.
20. Chaffanet M, Chauvin C, Laine M, et al. EGF receptor amplification and expression in human brain tumours. Eur J Cancer 1992; 28: 11-7.

21. Huang S M, Harari P M. Epidermal growth factor receptor inhibition in cancer therapy: biology, rationale and preliminary clinical results. Investigational new drugs 1999; 17: 259-69.
22. Rasheed B K, Wiltshire R N, Bigner S H, Bigner D D. Molecular pathogenesis of malignant gliomas. Current opinion in oncology 1999; 11: 162-7.
23. Wikstrand C J, Reist C J, Archer G E, Zalutsky M R, Bigner D D. The class III variant of the epidermal growth factor receptor (EGFRvIII): characterization and utilization as an immunotherapeutic target. Journal of neurovirology 1998; 4: 148-58.
24. Sugawa N, Ekstrand A J, James C D, Collins V P. Identical splicing of aberrant epidermal growth factor receptor transcripts from amplified rearranged genes in human glioblastomas. Proceedings of the National Academy of Sciences of the United States of America 1990; 87: 8602-6.
25. Batra S K, Castelino-Prabhu S, Wikstrand C J, et al. Epidermal growth factor ligand-independent, unregulated, cell-transforming potential of a naturally occurring human mutant EGFRvIII gene. Cell Growth Differ 1995; 6: 1251-9.
26. Humphrey P A, Wong A J, Vogelstein B, et al. Anti-synthetic peptide antibody reacting at the fusion junction of deletion-mutant epidermal growth factor receptors in human glioblastoma. Proceedings of the National Academy of Sciences of the United States of America 1990; 87: 4207-11.
27. Sok J C, Coppelli F M, Thomas S M, et al. Mutant epidermal growth factor receptor (EGFRvIII) contributes to head and neck cancer growth and resistance to EGFR targeting. Clin Cancer Res 2006; 12: 5064-73.
28. Wikstrand C J, Hale L P, Batra S K, et al. Monoclonal antibodies against EGFRvIII are tumor specific and react with breast and lung carcinomas and malignant gliomas. Cancer research 1995; 55: 3140-8.
29. Nagane M, Levitzki A, Gazit A, Cavenee W K, Huang H J. Drug resistance of human glioblastoma cells conferred by a tumor-specific mutant epidermal growth factor receptor through modulation of Bcl-XL and caspase-3-like proteases. Proceedings of the National Academy of Sciences of the United States of America 1998; 95: 5724-9.
30. Boskovitz A, Pegram, C, Peixoto, K, Zalutsky, M. R. and Bigner, D. D. Pre-clinical evaluation of D2C7, a monoclonal antibody reactive for both the wild type and variant III mutant epidermal growth factor receptor, for radioimmunotherapy of malignant gliomas World federation of neuro-oncology second quadrennial meeting and the sixth meeting of the european association for neuro-oncology. Edinburgh, United Kingdom; 2005.
31. Merlino G T, Xu Y H, Ishii S, et al. Amplification and enhanced expression of the epidermal growth factor receptor gene in A431 human carcinoma cells. Science (New York, N.Y. 1984; 224: 417-9.
32. Buchner J, Pastan I, Brinkmann U. A method for increasing the yield of properly folded recombinant fusion proteins: single-chain immunotoxins from renaturation of bacterial inclusion bodies. Analytical biochemistry 1992; 205: 263-70.
33. Beers R, Chowdhury P, Bigner D, Pastan I. Immunotoxins with increased activity against epidermal growth factor receptor vIII-expressing cells produced by antibody phage display. Clin Cancer Res 2000; 6: 2835-43.
34. Friedman H S, Houghton P J, Schold S C, Keir S, Bigner D D. Activity of 9-dimethylaminomethyl-10-hydroxycamptothecin against pediatric and adult central nervous system tumor xenografts. Cancer chemotherapy and pharmacology 1994; 34: 171-4.
35. Reiter Y, Brinkmann U, Lee B, Pastan I. Engineering antibody Fv fragments for cancer detection and therapy: disulfide-stabilized Fv fragments. Nature biotechnology 1996; 14: 123945.
36. Laskin J J, Sandler A B. Epidermal growth factor receptor: a promising target in solid tumours. Cancer treatment reviews 2004; 30: 1-17.
37. Brady L W, Miyamoto C, Woo D V, et al. Malignant astrocytomas treated with iodine-125 labeled monoclonal antibody 425 against epidermal growth factor receptor: a phase II trial. International journal of radiation oncology, biology, physics 1992; 22: 225-30.
38. Epenetos A A, Courtenay-Luck N, Pickering D, et al. Antibody guided irradiation of brain glioma by arterial infusion of radioactive monoclonal antibody against epidermal growth factor receptor and blood group A antigen. British medical journal (Clinical research ed 1985; 290: 1463-6.
39. Kalofonos H P, Pawlikowska T R, Hemingway A, et al. Antibody guided diagnosis and therapy of brain gliomas using radiolabeled monoclonal antibodies against epidermal growth factor receptor and placental alkaline phosphatase. J Nucl Med 1989; 30: 1636-45.
40. Quang T S, Brady L W. Radioimmunotherapy as a novel treatment regimen: 125I-labeled monoclonal antibody 425 in the treatment of high-grade brain gliomas. International journal of radiation oncology, biology, physics 2004; 58: 972-5.
41. Sampson J H, Akabani G, Archer G E, et al. Intracerebral infusion of an EGFR-targeted toxin in recurrent malignant brain tumors. Neuro-oncology 2008; 10: 320-9.
42. Kuan C T, Reist C J, Foulon C F, et al. 125I-labeled anti-epidermal growth factor receptor-vIII single-chain Fv exhibits specific and high-level targeting of glioma xenografts. Clin Cancer Res 1999; 5: 1539-49.
43. Kuan C T, Wikstrand C J, Archer G, et al. Increased binding affinity enhances targeting of glioma xenografts by EGFRvIII-specific scFv. International journal of cancer 2000; 88: 962-9.
44. Reist C J, Archer G E, Kurpad S N, et al. Tumor-specific anti-epidermal growth factor receptor variant III monoclonal antibodies: use of the tyramine-cellobiose radioiodination method enhances cellular retention and uptake in tumor xenografts. Cancer research 1995; 55: 4375-82.
45. Schmidt M, Maurer-Gebhard M, Groner B, Kohler G, Brochmann-Santos G, Wels W. Suppression of metastasis formation by a recombinant single chain antibody-toxin targeted to full-length and oncogenic variant EGF receptors. Oncogene 1999; 18: 1711-21.
46. Wikstrand C J, McLendon R E, Friedman A H, Bigner D D. Cell surface localization and density of the tumor-associated variant of the epidermal growth factor receptor, EGFRvIII. Cancer research 1997; 57: 4130-40.
47. Frederick L, Wang X Y, Eley G, James C D. Diversity and frequency of epidermal growth factor receptor mutations in human glioblastomas. Cancer research 2000; 60: 1383-7.
48. Masui H, Kawamoto T, Sato J D, Wolf B, Sato G, Mendelsohn J. Growth inhibition of human tumor cells in athymic mice by anti-epidermal growth factor receptor monoclonal antibodies. Cancer research 1984; 44: 1002-7.

49. Perera R M, Narita Y, Furnari F B, et al. Treatment of human tumor xenografts with monoclonal antibody 806 in combination with a prototypical epidermal growth factor receptor-specific antibody generates enhanced anti-tumor activity. Clin Cancer Res 2005; 11: 6390-9.
50. Johns T G, Stockert E, Ritter G, et al. Novel monoclonal antibody specific for the de2-7 epidermal growth factor receptor (EGFR) that also recognizes the EGFR expressed in cells containing amplification of the EGFR gene. International journal of cancer 2002; 98: 398-408.
51. Scott A M, Lee F T, Tebbutt N, et al. A phase I clinical trial with monoclonal antibody ch806 targeting transitional state and mutant epidermal growth factor receptors. Proceedings of the National Academy of Sciences of the United States of America 2007; 104: 4071-6.

The invention claimed is:

1. A therapeutic, anti-tumor, single chain variable region antibody which binds with a binding affinity that is at least $5 \times 10^8$ $M^{-1}$ as measured by surface plasmon resonance to both (a) EGFR found on normal human cells and (b) EGFR variant III mutant, wherein the single chain variable region antibody is cloned from a hybridoma producing monoclonal antibody D2C7, wherein the single chain variable region antibody is covalently linked to a cytotoxic agent which is a form of *Pseudomonas* exotoxin A.

2. The therapeutic, anti-tumor, single chain variable region antibody of claim 1 wherein the cytotoxic agent and the single chain variable region antibody are constituents of a fusion protein.

3. The therapeutic, anti-tumor, single chain variable region antibody of claim 1 wherein the cytotoxic agent comprises a KDEL peptide.

4. The therapeutic, anti-tumor, single chain variable region antibody of claim 1 wherein the single chain variable region antibody comprises a VH sequence as shown in SEQ ID NO: 1.

5. The therapeutic, anti-tumor, single chain variable region antibody of claim 1 wherein the single chain variable region antibody comprises a VL sequence as shown in SEQ ID NO: 2.

6. The therapeutic, anti-tumor, single chain variable region antibody of claim 1 wherein the single chain variable region antibody comprises CDR1, CDR2, and CDR3 regions as shown in SEQ ID NO: 3, 4, 5, 6, 7, and 8.

7. The therapeutic, anti-tumor, single chain variable region antibody of claim 1 which is disulfide stabilized.

8. A therapeutic, anti-tumor, fusion protein comprising (a) a single chain variable region antibody which binds to both (i) EGFR found on normal human cells and (ii) EGFR variant III mutant, wherein the single chain variable region antibody is cloned from a hybridoma producing monoclonal antibody D2C7; and (b) a cytotoxic agent which is a form of *Pseudomonas* exotoxin A.

9. The therapeutic, anti-tumor, fusion protein of claim 8 which is disulfide stabilized.

10. The therapeutic, anti-tumor, fusion protein of claim 8 wherein the cytotoxic agent comprises a KDEL peptide.

11. The therapeutic, anti-tumor, fusion protein of claim 8 wherein the single chain variable region antibody comprises a VH sequence as shown in SEQ ID NO: 1.

12. The therapeutic, anti-tumor, fusion protein of claim 8 wherein the single chain variable region antibody comprises a VL sequence as shown in SEQ ID NO: 2.

13. The therapeutic, anti-tumor, fusion protein of claim 8 wherein the single chain variable region antibody comprises CDR1, CDR2, and CDR3 regions as shown in SEQ ID NO: 3, 4, 5, 6, 7, and 8.

* * * * *